US008968348B2

(12) United States Patent
DiCaprio

(10) Patent No.: US 8,968,348 B2
(45) Date of Patent: Mar. 3, 2015

(54) BALLOON DELIVERY APPARATUS AND METHOD FOR USING AND MANUFACTURING THE SAME

(75) Inventor: Fernando DiCaprio, St. Paul, MN (US)

(73) Assignee: Svelte Medical Systems, Inc., New Providence, NJ (US)

( * ) Notice: Subject to any disclaimer, the term of this patent is extended or adjusted under 35 U.S.C. 154(b) by 30 days.

(21) Appl. No.: 13/224,037

(22) Filed: Sep. 1, 2011

(65) Prior Publication Data

US 2012/0053604 A1 Mar. 1, 2012

Related U.S. Application Data

(63) Continuation of application No. PCT/US2010/028581, filed on Mar. 25, 2010.

(60) Provisional application No. 61/163,103, filed on Mar. 25, 2009.

(51) Int. Cl.
| A61M 29/02 | (2006.01) |
| A61F 2/958 | (2013.01) |
| A61M 25/10 | (2013.01) |
| A61M 25/01 | (2006.01) |

(52) U.S. Cl.
CPC .............. *A61M 25/104* (2013.01); *A61F 2/958* (2013.01); *A61M 25/1027* (2013.01); *A61M 25/0102* (2013.01); *A61M 2025/0186* (2013.01); *A61M 2025/1079* (2013.01); *A61M 2025/1093* (2013.01)
USPC ........................... 606/192; 606/194; 623/1.11

(58) Field of Classification Search
CPC ............ A61M 25/0025; A61M 25/10; A61M 25/104; A61M 25/1027; A61B 17/12022; A61B 17/12136; A61B 2017/22001; A61F 2/958

USPC .................. 623/1.11, 1.12; 606/191, 194
See application file for complete search history.

(56) References Cited

U.S. PATENT DOCUMENTS

| 5,318,529 A | * | 6/1994 | Kontos ........................... 606/194 |
| 5,409,495 A | | 4/1995 | Osborn | |

(Continued)

FOREIGN PATENT DOCUMENTS

EP         1208815 A2      5/2002

OTHER PUBLICATIONS

International Search Report for Application PCT/US2010/028581 dated Jun. 2, 2010.

(Continued)

*Primary Examiner* — Kathleen Holwerda
*Assistant Examiner* — Sarah W Aleman
(74) *Attorney, Agent, or Firm* — Honigman Miller Schwartz and Cohn LLP

(57) ABSTRACT

A balloon delivery catheter apparatus including a catheter tubing defining a lumen therethrough, a balloon disposed near a distal end of the catheter tubing and moving between deflated and inflated states, and a core wire having a proximal end attached to the catheter tubing inside the lumen and extending distally away and substantially co-axially with the catheter tubing through the balloon to a distal free end. Proximal and distal balloon control bands are concentrically arranged around respective proximal and distal end portions of the balloon. A coil disposed around the core wire has a proximal end attached to at least one of the distal end portion of the balloon and the distal balloon control band.

75 Claims, 13 Drawing Sheets

(56) References Cited

U.S. PATENT DOCUMENTS

| | | | |
|---|---|---|---|
| 5,606,981 A * | 3/1997 | Tartacower et al. | 600/585 |
| 5,702,364 A * | 12/1997 | Euteneuer et al. | 606/192 |
| 5,810,871 A * | 9/1998 | Tuckey et al. | 606/198 |
| 5,968,069 A * | 10/1999 | Dusbabek et al. | 606/194 |
| 6,071,285 A | 6/2000 | Lashinski et al. | |
| 6,375,660 B1 * | 4/2002 | Fischell et al. | 606/108 |
| 6,562,061 B1 | 5/2003 | Wang et al. | |
| 6,585,747 B1 | 7/2003 | Limon et al. | |
| 7,367,982 B2 | 5/2008 | Nash et al. | |
| 2002/0147491 A1 | 10/2002 | Khan et al. | |
| 2003/0074044 A1 * | 4/2003 | Randby et al. | 623/1.11 |
| 2005/0054951 A1 * | 3/2005 | Parins | 600/585 |
| 2008/0077223 A1 | 3/2008 | Fischell et al. | |
| 2008/0228171 A1 | 9/2008 | Kugler et al. | |
| 2008/0312671 A1 | 12/2008 | Riles et al. | |

OTHER PUBLICATIONS

U.S. Patent and Trademark Office Non-Final Office Action dated Jan. 17, 2013, relating to U.S. Appl. No. 12/969,189.

European Search Report for Application No. 10756822 dated Nov. 2, 2012.

\* cited by examiner

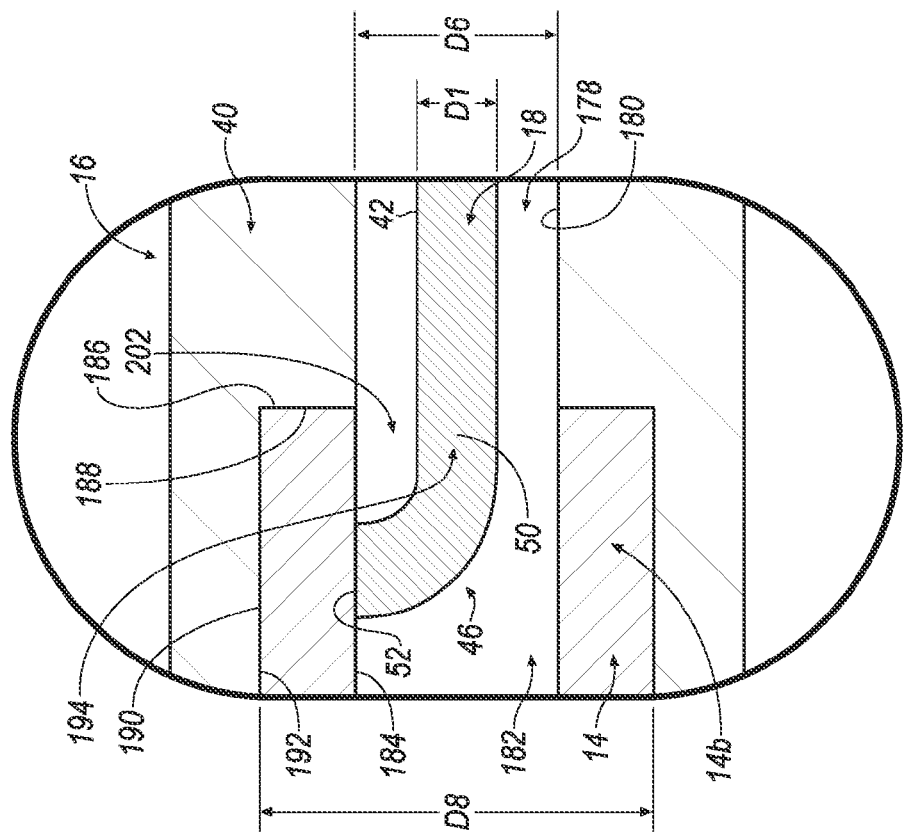
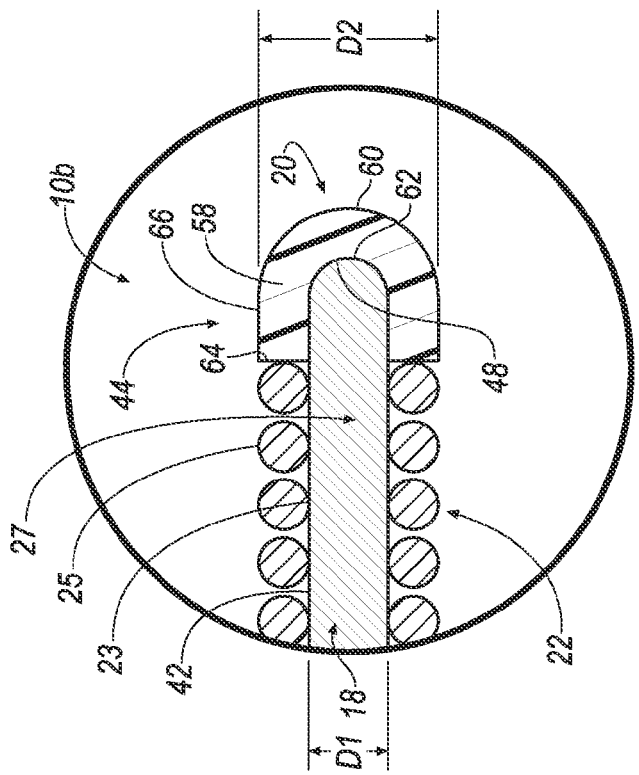
FIG. 4
FIG. 3

BALLOON DELIVERY APPARATUS AND METHOD FOR USING AND MANUFACTURING THE SAME

CROSS REFERENCE TO RELATED APPLICATIONS

This U.S. patent application under 35 U.S.C. §111(a) is a continuation of, and claims priority under 35 U.S.C. §120 and §365(c) from, PCT Patent Application PCT/US2010/28581, having an international filing date of Mar. 25, 2010, which claims priority under 35 U.S.C. §119(e) to U.S. Provisional Application 61/163,103, filed on Mar. 25, 2009. The disclosures of these prior applications are considered part of the disclosure of this application and are hereby incorporated by reference in their entireties.

TECHNICAL FIELD

This disclosure relates to balloon catheter delivery apparatuses and methods for using and manufacturing the same.

BACKGROUND

Balloon deliver apparatuses, or angioplasty balloons, are useful for treating maladies in patients that involve the patients' vasculature. For example, angioplasty balloon dilation is sometimes used for the treatment of stenosis, wherein a small balloon is disposed at the location of the stenosis and inflated to expand the stenosis in a vessel lumen and improve the vessel's patency. Angioplasty balloons are also useful for deploying stents in a patient's vasculature that maintain the vessel's locally expanded state or patency and prevent restenosis. It is noted that coronary stenting is believed to reduce restenosis rates in patients when compared with conventional balloon dilation. Amer. J. Cardio. 2002, 90, 1187-1192.

In either balloon angioplasty or stenting procedures, angioplasty balloons are typically used to expand a stenosis in a patient's vasculature. In procedures including the deployment of a stent, the angioplasty balloon may also expand and deploy the stent within the patient's vasculature. These procedures are traditionally preceded by the placement of a guidewire through the stenosis, which is followed by angioplasty balloon dilation at the stenosis with a balloon angioplasty catheter that has been advanced over the guidewire. The balloon angioplasty catheter is then withdrawn from the patient and a stent delivery system that includes the stent is advanced over the guidewire, and the stent is then deployed at the site of the dilated stenosis.

Conventional stenting procedures include the following steps:
1. Place coronary guidewire into wire introducer;
2. Load guidewire into guiding catheter;
3. Advance guidewire across lesion;
4. Remove wire introducer;
5. Load predilatation balloon angioplasty catheter onto guidewire;
6. Advance balloon catheter into guiding catheter;
7. Cross lesion with predilatation balloon;
8. Dilate lesion with balloon;
9. Angiography;
10. Remove predilatation balloon catheter;
11. Load stent delivery system (SDS) onto guidewire;
12. Advance SDS into guiding catheter;
13. Cross lesion with SDS;
14. Deploy stent at high pressure;
15. Angiography; and
16. Remove delivery system.

Because of the complexity of the procedure, conventional stenting often involves lengthy procedural times, prolonged exposure to radiation, lengthy administration of contrast agents, and great expense. J. Amer. Col. Cardio. 1999, 34, 1910-1915. Furthermore, the balloon predilation followed by stent placement often leads to major vascular trauma in a patient.

SUMMARY

The disclosure provides an apparatus and methods that improve the treatment of stenosis in a patient when compared with conventional stenting treatments. The apparatus and the methods of using the apparatus reduce vascular trauma in a patient, reduce procedural time, reduce a patient's exposure to radiation, reduce the administration of a contrast agent, and reduce costs using direct stenting procedures.

The disclosed apparatus and methods may concern direct stenting procedures for treating stenosis. Direct stenting using the apparatus and/or methods may generally involve the following steps:
1. Placing a peel away introducer over distal end of stent delivery system;
2. Loading a stent delivery system into a guiding catheter and removing the peel away introducer;
3. Advancing the stent delivery system across lesion;
4. Dilating a balloon of the delivery system and deploying the stent at high pressure;
5. Angiography; and
6. Removing the delivery system.

Thus, direct stenting using the apparatus and/or methods offers fewer steps than conventional stenting; and consequently, procedural times are often reduced by 20-30%, the patient's radiation exposure (e.g., Fluoroscopy Time) is reduced by 20-30%, and the procedural cost is often reduced by 22-35%. Some implementations may provide some patients with a reduced incidence of restenosis and/or a reduced MACE rate. It is also noted that the omission of the predilation step in direct stenting is believed to reduce vessel wall damage and distal embolization compared with conventional stenting. See e.g., J. Amer. Coll. Cardio. 2008, 51, 1060-1065.

One aspect of the disclosure provides a balloon delivery catheter that includes a catheter tubing having a balloon near the distal end of the catheter tubing. The balloon includes a distal end, a proximal end, and an intermediate segment. The balloon is nested between a distal balloon control band and a proximal balloon control band. A core wire extends throughout a portion of the catheter and includes a proximal portion and a distal portion in which the distal portion of the core wire includes a coiled section that extends beyond the distal end of the balloon. In some implementations, the balloon delivery catheter further includes a stent disposed around the balloon such that when the balloon is inflated the inflated balloon expands the stent so that a radius of the stent is increased. In some examples, the catheter includes a distal balloon control band having a portion (e.g., the proximal end of the distal control band) that has a larger profile (e.g., a larger diametric cross section) than that of the unexpanded stent, so that when the balloon and stent are advanced to a stenosis site, the distal balloon control band pushes through the stenosis leaving a channel having a size sufficient for the stent. Moreover, the larger profile distal balloon control band may prevent any of the stent edges from catching on previously deployed stents thereby improving stent crossing in a patient's vasculature. In conventional catheter systems, the balloon material distal to the stent can be compressed as it is advanced into the stenosis and the distal edge of the stent can catch or engage a narrowed vessel wall or occlusion as it passes through the stenosis. These problems are advantageously avoided using the disclosed catheter, which includes a stent and a distal balloon control band having a larger profile than the stent, because the stent does not have and does not develop any exposed edges during its advancement into the stenosis. Consequently, the stent does not typically catch on the narrowed vessel walls or occlusion causing the stenosis.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 3 is an enlarged view of a portion of the distal shaft portion indicated by line 3 of FIG. 2.

FIG. 4 is an enlarged view of a portion of the distal shaft portion indicated by line 4 of FIG. 2.

Like reference symbols in the various drawings indicate like elements.

DETAILED DESCRIPTION

Figure 1:
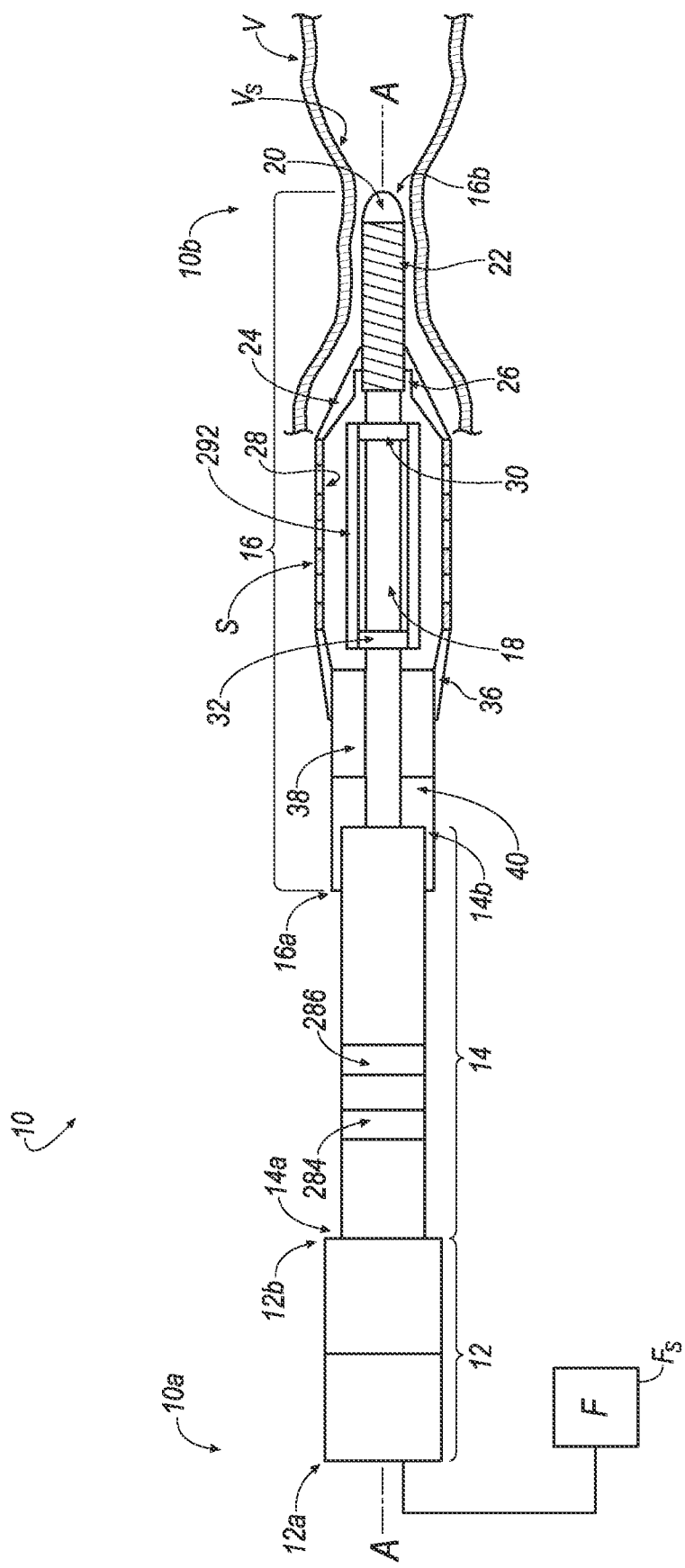
FIG. 1 is a side view of a balloon catheter delivery apparatus, in which the distal shaft portion is shown in partial longitudinal-sectional view for illustrative purposes.

The present disclosure relates generally to a balloon catheter delivery apparatus that is useful for treating stenosis in a patient.

I. Definitions

As used herein, the terms "catheter" or "catheter tubing" are used interchangeably and refer to a tube that sized and shaped to be inserted into a body cavity, duct, or vessel. Some catheters are formed of a distal portion and a proximal portion wherein the proximal portion is a hypotube, and the distal portion is a distal flexible tube. Catheters may have diameters of from about 0.3 mm to about 2.4 mm and lengths of from about 70 cm to about 170 cm.

As used herein, the terms "catheter hypotube" or "hypotube" are used interchangeably and refer to a small metallic tube that often forms the proximal portion of a catheter. Hypotubes are generally sized and shaped to be inserted into a body cavity, duct, or vessel. For example, may have outer diameters of from about 0.3 mm to about 2.4 mm, and lengths of from about 50 cm to about 140 cm (e.g., from about 70 cm to about 120 cm). Metallic hypotubes may be treated (e.g., coated, polished, sterilized, any combination thereof, or the like) to improve its utility as a portion of a catheter.

As used herein, a "distal flexible tube" is a component of a catheter located distal to a proximal portion. In some examples, the distal flexible tube has a greater flexibility than the proximal portion of the catheter. In some implementations, the distal flexible tube is formed from a polymer such as silicone rubber. In other implementations, the distal flexible tube has a diameter of from about 0.3 mm to about 2.4 mm, and a length of from about 0.5 cm to about 20 cm (e.g., from about 1 cm to about 10 cm).

As used herein, the terms "core wire" and "guide wire" are used interchangeably and refer to a small wire that extends from a distal tip of a catheter hypotube. In many instances, the distal tip of the core wire has a curved or rounded surface to inhibit its tendency to pierce or dissect a blood vessel.

As used herein, the term "balloon" and "balloon member" are used interchangeably and refer to a flexible inflatable container capable of increasing its volume upon inflation with a fluid and decreasing its volume upon deflation.

As used herein, "stainless steel" refers to any steel alloy with a minimum of about 10.5% chromium content by mass. It is noted that stainless steel may be coated or otherwise treated to enhance one or more of its physical properties. For instance, stainless steel may be coated with a polymer such as PTFE to reduce its coefficient of friction or improve is chemical resistance.

As used herein, "PTFE" and "polytetrafluoroethylene" are used interchangeably and refer to a synthetic fluoropolymer of tetrafluoroethylene. One such polymer is known by the DuPont brand name Teflon.

As used herein, "silicone rubber" refers to any rubber-like material composed of silicone, carbon, hydrogen, or oxygen. In several instances, silocone rubber comprises a Si—O—Si polymer backbone. Exemplary silicone rubbers include polymethylsiloxane, polyethylsiloxane, polypropylsiloxane, any combination thereof, or the like.

As used herein, "depth marker", "optical marker", and "marker" are used interchangeably and refer to optically visible marks that identify a given length or desired location on the catheter hypotube or the core wire. Some optical markers are observable in X-Ray scans of the catheter hypotube or core wire on which they are located. Other markers are optically observable by the human eye under visible light conditions. Optical markers may include painted markers or structural markers that attach to the catheter hypotube or the core wire (e.g., bands, notches, blocks, or the like).

As used herein, "affix" and "affixed" refer to the attachment of one object to another. Affixing includes bonding, welding, crimping, or otherwise adhering or attaching one object to another object.

II. Apparatus

The apparatus and methods offer several advantages over traditional balloon angioplasty and conventional stenting, for example, by providing a balloon delivery catheter that includes a catheter tubing having a balloon near the distal end of the catheter tubing. The balloon includes a distal end, a proximal end, and an intermediate segment. The balloon can be nested between a distal balloon control band and a proximal balloon control band. The catheter may include core wire extending throughout a portion of the catheter and including a proximal portion and a distal portion in which the distal portion of the core wire includes a coiled section that extends beyond the distal end of the balloon. The catheter may reduce vasculature trauma experienced by a patient when compared with conventional balloon angioplasty or conventional stenting, because the proximal and distal balloon control bands restrict longitudinal overexpansion of the balloon during inflation. This restriction in overexpansion of the balloon affected by the balloon control bands may reduce the trauma to the patient's vasculature and reduce the incidence of restenosis.

Figure 13:
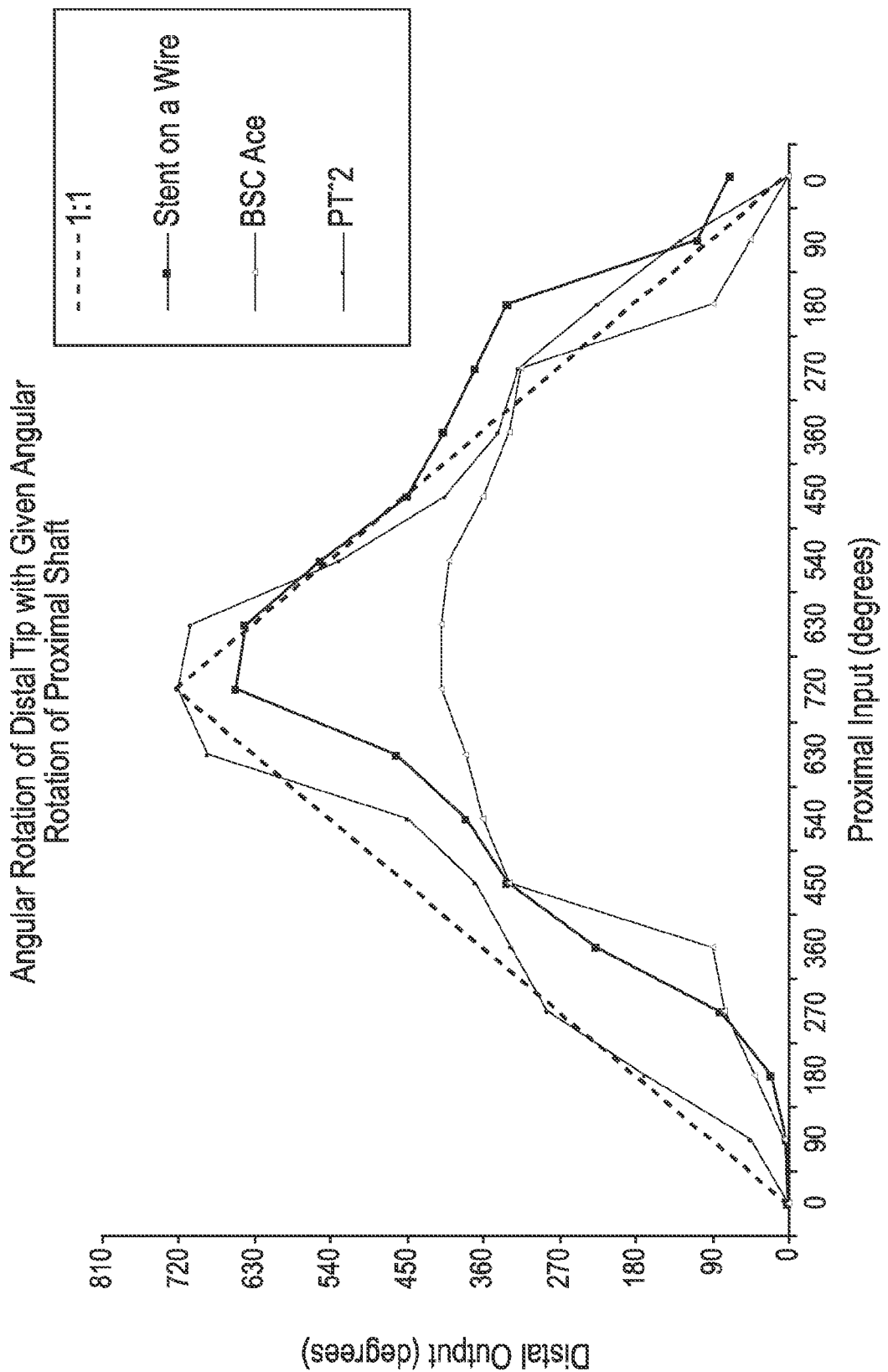
FIG. 13 is a plot of distal output (in degrees) as a function of proximal input (in degrees) for an exemplary balloon catheter delivery apparatus.
Figure 14:
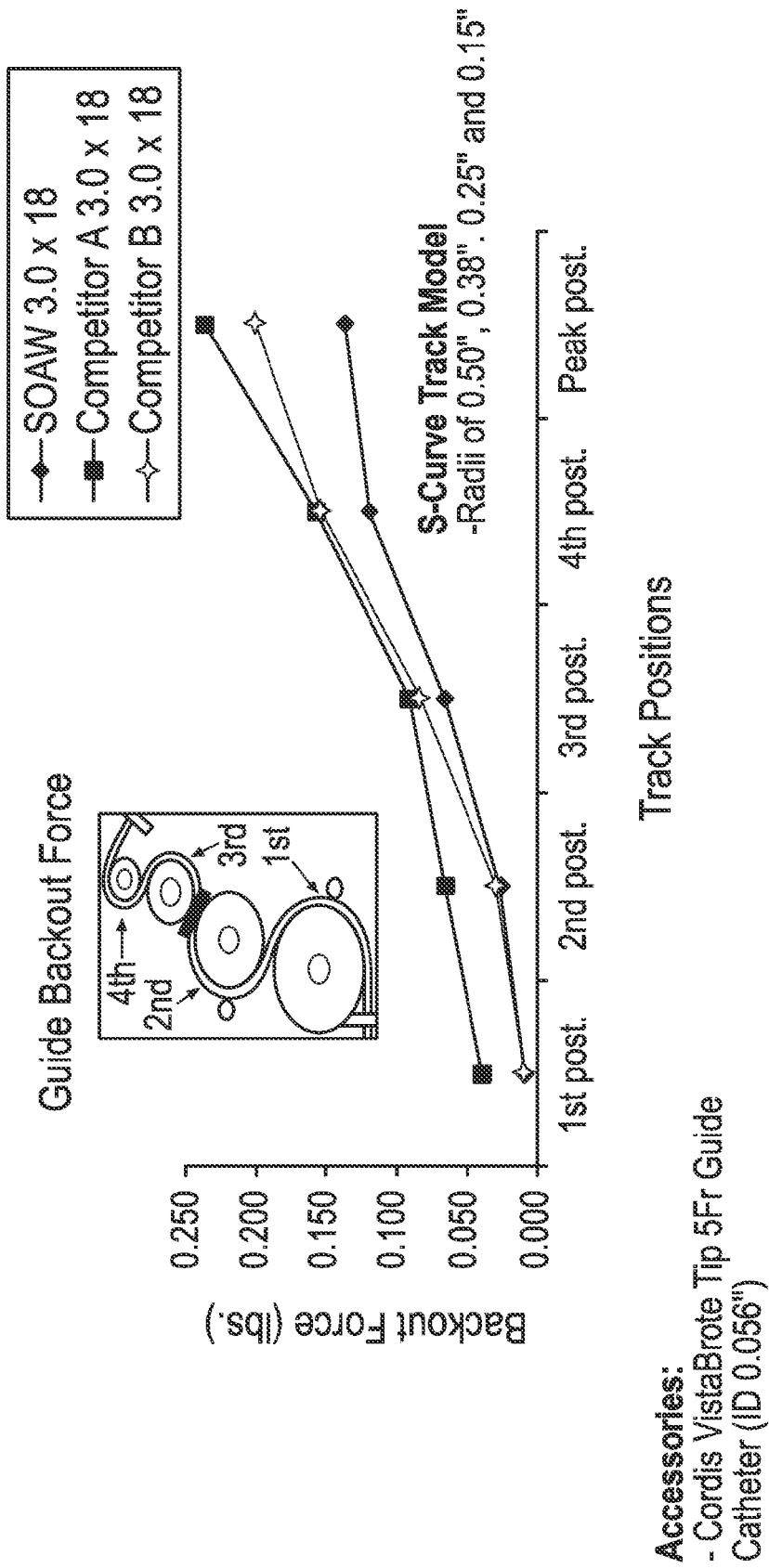
FIG. 14 is a plot of back-out force as a function of track position in an S-curve track, demonstrating that the apparatus is highly maneuverable in a patient's vasculature.

Referring to FIGS. 13 and 14, the balloon delivery catheter may provide improved control and flexibility, which provides improved maneuverability through a patient's vasculature. FIG. 13 demonstrates that the disclosed apparatus can provide excellent rotational responsiveness to a user's input rotation, and FIG. 14 demonstrates that the disclosed apparatus has excellent flexibility and can be withdrawn from bends around a series of alternating curves without the need of excessive force.

In some implementations, the balloon delivery catheter optionally includes a stent disposed around a balloon such that when the balloon is inflated, the inflated balloon expands the stent so that a radius of the stent increases. In some examples, the distal balloon control band includes at least a portion that has a greater profile, i.e., diametric cross section $DC_A$, than the unexpanded stent disposed about the balloon. These implementations may reduce the likelihood that the stent snags on a vessel wall or other occlusion at the stenosis site, because the larger profile distal control band pushes through the stenosis before the stent and creates a channel of suitable size for accepting the stent. Moreover, these implementations may reduce the likelihood that the leading edge of the stent snags on a vessel wall, a previously deployed stent, or other occlusion in the patient's vasculature, because the larger profile distal balloon control band reduces or altogether eliminates any exposed leading edges on the stent that could catch on previously deployed stents or vessel wall in a patient's vasculature. In addition, the constriction applied at the ends of the balloon by the balloon control bands retract the balloon to a minimum diameter so that the apparatus does not snag the stent upon withdrawal of the apparatus from the patient.

A balloon delivery catheter apparatus may include an all-in-one stent delivery system comprising a fixed guide wire and a catheter including an elongate flexible hypotube having distal and proximal shaft portions and an inflatable balloon to which a stent may optionally be affixed thereto. The balloon may be in fluid communication with the lumen of the flexible hypotube. In some examples, the proximal end of the core wire is affixed to the distal end of the proximal shaft portion of the catheter hypotube and the distal tip of the core wire extends beyond the balloon. The balloon has a proximal end attached to the distal section of the hypotube and a distal end attached to the core wire at a location proximal to the distal tip of the wire. The apparatus may include balloon control bands that assist in stent deployment and/or vessel expansion by constricting dilation of the balloon at its proximal and distal ends, thereby encouraging the balloon midsection beneath the stent (if a stent is affixed to the balloon) to inflate and deploy at the middle before the ends expand. In embodiments comprising the optional stent, the balloon control bands restrict the overexpansion of the balloon and the stent affixed thereto at their respective ends—an event that often causes trauma to vessel walls. This restriction in overexpansion of the balloon caused by balloon control bands may reduce the incidence of restenosis in the patient. In addition, the constriction applied at the ends of the balloon by the balloon control bands retract the balloon to a minimum diameter so that the apparatus does not snag the stent upon removal from the patient. In various examples, the profile of the apparatus may be minimized not only by the balloon control bands, but also by the various connections within the apparatus, many of the components being directly bonded to one another, for example, but not limited to, laser welding.

FIG. 1 provides a part side view, part longitudinal-sectional illustrative view of a balloon catheter delivery apparatus 10, which may also be referred to as a stent-on-a-wire (SOAW) delivery catheter. The delivery apparatus 10 may be sterilized by an ethylene oxide gas, radiation treatment (e.g., treatment with e-beam or gamma radiation), sterilizing solution, any combination thereof, or other sterilizing medium or procedure compatible with the materials used in the balloon catheter delivery apparatus.

Although the foregoing description discloses a balloon catheter delivery apparatus 10 that may be used for placing a stent S at, for example, a stenosis $V_S$ of a vessel V in, for example, a patient, (e.g., a human), other uses are possible. Accordingly, in some implementations, the delivery apparatus 10 may be utilized to treat, for example, ischemic heart disease. Further, the delivery apparatus 10 may also find utility as an angioplasty catheter that does not include a stent S or the stent S may be removably affixed to the balloon catheter delivery apparatus 10.

The delivery apparatus 10 may be used for placing an angioplasty balloon catheter through a stenosis $V_S$. The structure of delivery apparatus 10 may enhance, for example, the pushability of an angioplasty catheter that is utilized for dilating a stenosis $V_S$.

Figure 11:
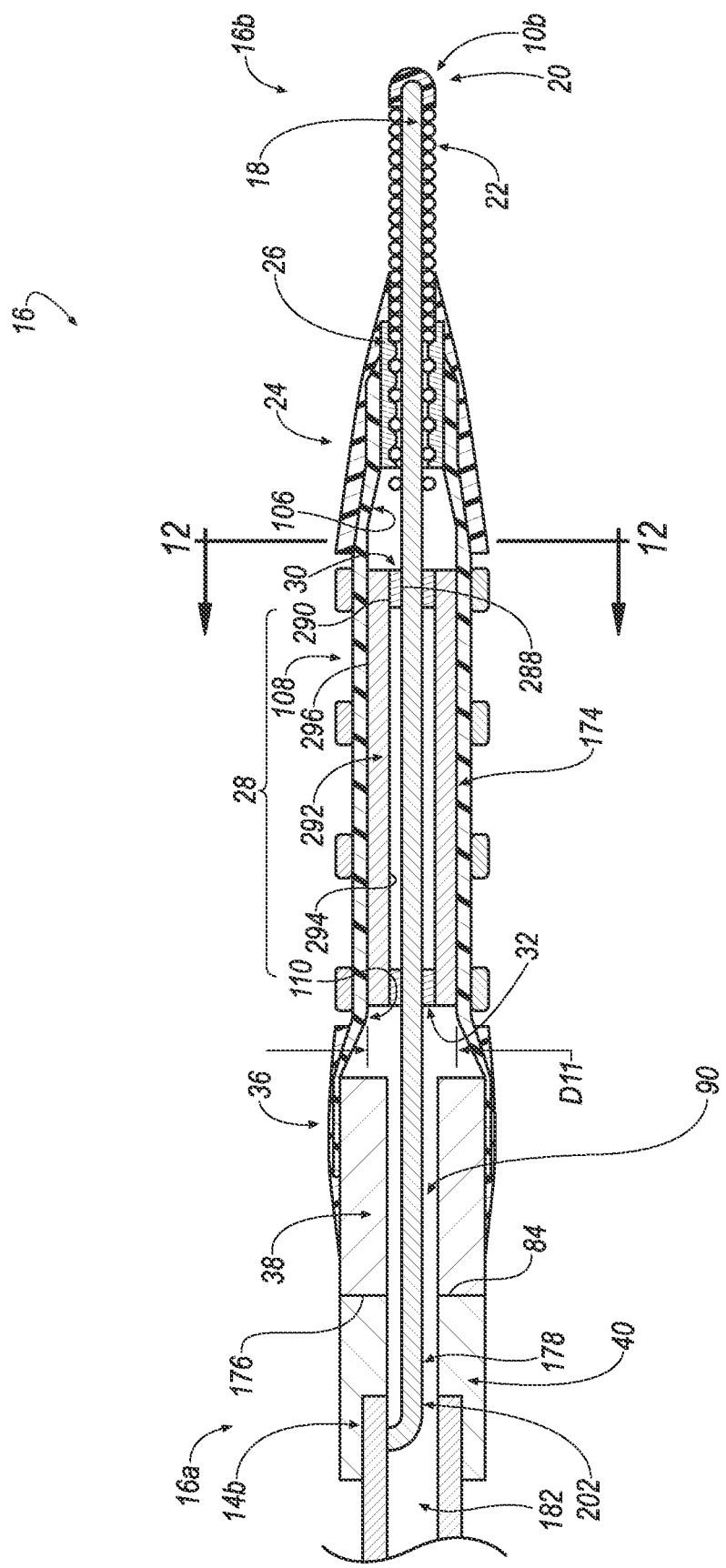
FIG. 11 is a longitudinal-sectional view of a distal shaft portion of the balloon catheter apparatus in an undeployed state.
Figure 12:
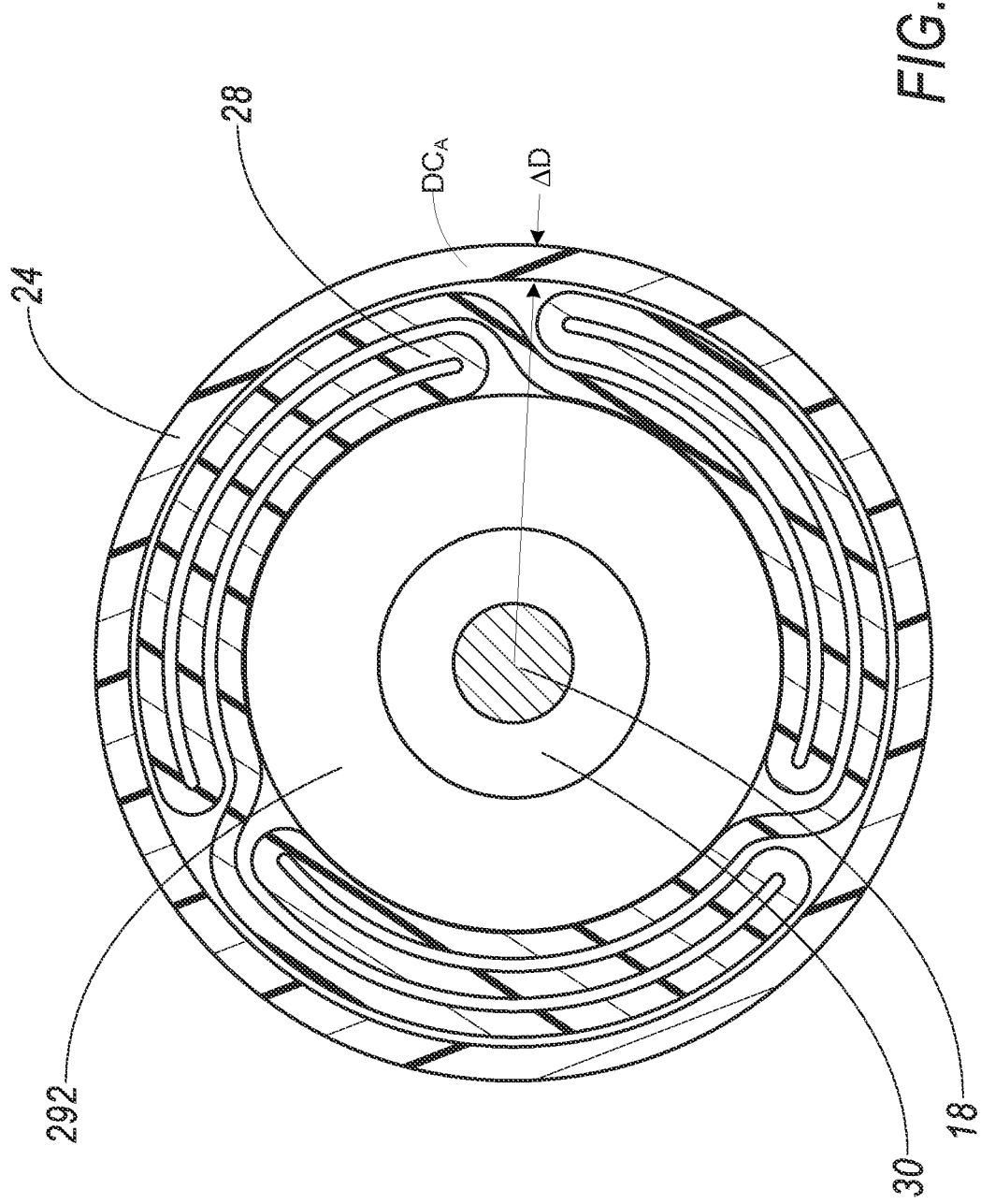
FIG. 12 is a cross-sectional illustration of the distal shaft taken at about line 12 of FIG. 11 and viewed in a proximal direction in accordance with an example embodiment of the invention.

A distal shaft portion 16 of the delivery apparatus 10 is shown in a slightly expanded or inflated state in the examples shown in FIGS. 1-7. The examples shown in FIGS. 11 and 12 illustrate the distal shaft portion 16 of the delivery apparatus 10 prior to inflation.

As seen in FIG. 1, an axis A-A extends through the delivery apparatus 10 from a proximal end 10a to a distal end 10b. The delivery apparatus 10 may optionally include a handle 12 having a proximal end 12a and a distal end 12b. The delivery apparatus 10 may also include a catheter hypotube that comprises a proximal shaft section 14 having a proximal end 14a and a distal end 14b. The catheter hypotube also comprises a proximal distal shaft portion 16 having a proximal end 16a and a distal end 16b.

The handle 12, the proximal shaft portion 14, and/or all or part of the distal shaft portion 16 may form a lumen or passage allowing for inflation of a balloon 28 of the delivery apparatus 10. The proximal end 14a of the proximal shaft portion 14 may be fixedly or removably connected to the distal end 12b of the handle 12. In some examples, the distal end 12b of the handle 12 is approximately 145 centimeters from the distal end 10b of the delivery apparatus 10. Moreover, the distal end 14b of the proximal shaft portion 14 may be fixedly or removably connected proximate to the proximal end 16a of the distal shaft portion 16. In some examples, the distal end 14b of the proximal shaft portion 14 is disposed within the distal shaft portion 16 proximate to the proximal end 16a of the distal shaft portion 16 (see e.g., FIG. 4). Alternatively, the proximal end 16a of the distal shaft portion 16 may be disposed within the distal end 14b of the proximal shaft portion 14. Other ways of connecting the handle 12, the proximal shaft portion 14 and the distal shaft portion 16 are possible as well.

In some implementations, the delivery apparatus 10 functions in a manner that permits the stent, S, to be removably attached to the distal shaft portion 16. Further, the distal shaft portion 16 may retain the stent S and later deploy the stent S at, for example, a stenosis $V_S$ of a vessel V of a human body. Upon deployment of the stent S, the delivery apparatus 10 may be said to no longer include or retain the stent S.

The handle 12 and the proximal shaft portion 14 may function in a manner that permits communication of a fluid F from a fluid source $F_S$ to the distal shaft portion 16. In some examples, the handle 12 functions in a manner that permits or denies movement of the fluid F into or out of the distal shaft portion 16 by way of the proximal shaft portion 14. The fluid F may be pressurized to between about 8 and about 16 atmospheres.

Figure 2:
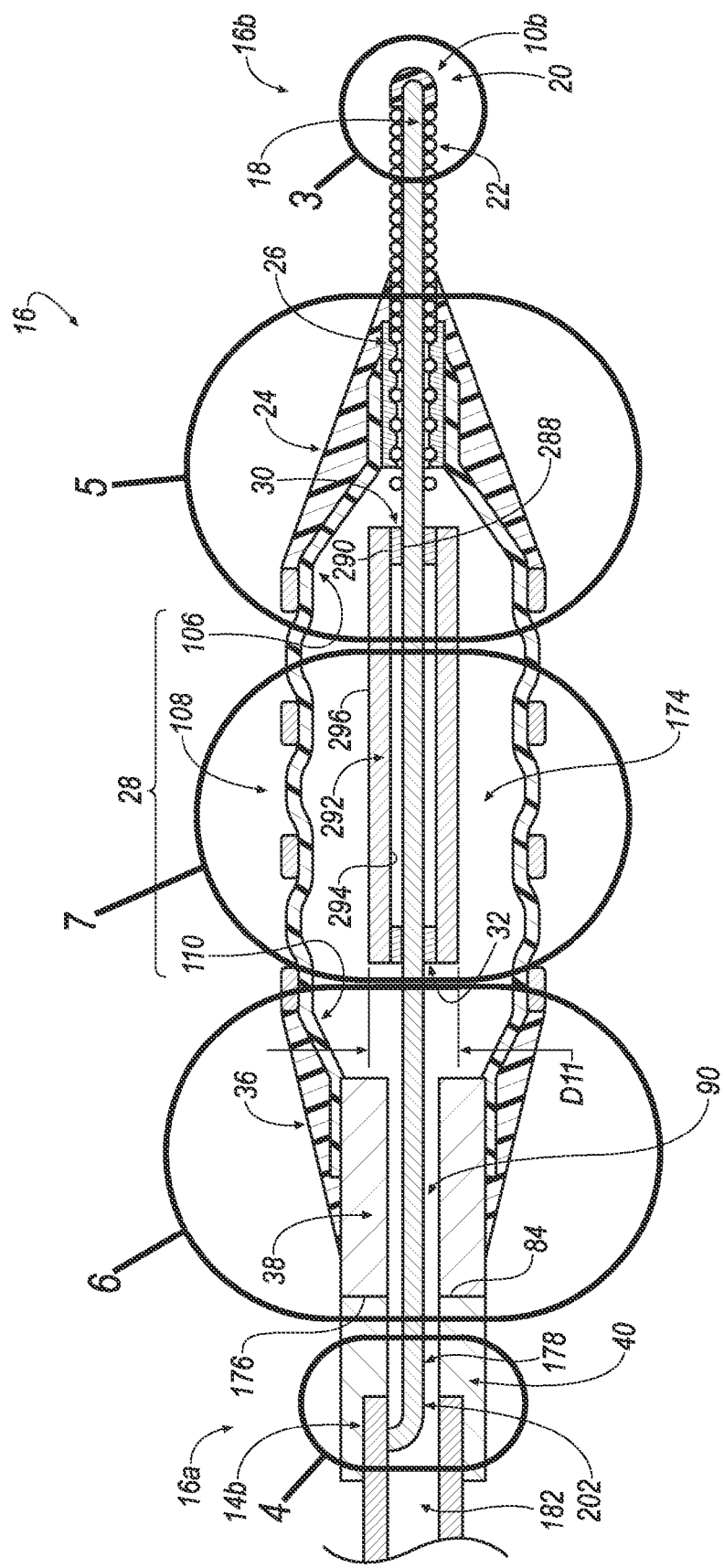
FIG. 2 is a longitudinal-sectional view of a distal shaft portion of the balloon catheter delivery apparatus of FIG. 1.

Referring to FIGS. 1 and 2, in some implementations, the distal shaft portion 16 includes an axial core wire 18, a capped distal tip member 20, a coil member 22, a distal balloon control band 24, a distal bonding portion 26, a balloon 28, a distal marker band 30, a proximal marker band 32, a proximal balloon control band 36, a distal shaft mounting portion 38 and a proximal shaft mounting portion 40.

Referring now to FIGS. 3 and 4, the core wire 18 may include a radial outer surface 42, a first, axial distal end segment 44 and a distal end surface 48 (see e.g., FIG. 3) and a second, axial proximal end segment 46 and a distal end surface 52 (see e.g., FIG. 4). As shown in FIGS. 1 and 2, in some examples, the distal end segment 44 of the core wire 18 may extend beyond the distal end of the balloon control band 24.

The radial outer surface 42 may define the core wire 18 to include a substantially circular cross-section having an outer diameter D1. The radial outer surface 42 is not limited, however, to defining the core wire 18 to include a substantially circular cross section and the core wire 18 may include any desirable cross-sectional shape, such as, for example, a square, rectangular, hexagonal cross-section or the like. In addition, the shape of the core wire 18 may not be uniform. For example, a portion of the core wire 18 within the capped distal tip member 58 may be substantially circular, while a portion of the core wire 18 that lies within the coil member 22 may be rectangular. The core wire 18 may taper as it extends axially from the proximal end 10a to the distal end 10b. The core wire 18 may also be coined. The tapering and coining of the core wire 18 may permit the core wire 18 to be flexible and/or shapeable.

As seen in FIGS. 2 and 3, the first axial, distal, end segment 44 of the core wire 18 may define, in part, a distal end 10b of the delivery apparatus 10. The first, axial distal end segment 44 may terminate in a rounded, substantially dome-shaped distal end surface 48. As seen in FIGS. 2 and 4, the second axial, proximal, end segment 46 of the core wire 18 may be located axially away from the distal end 10b of the delivery apparatus 10 at any desirable axial distance/length. The second axial proximal end segment 46 may terminate in a proximal end surface 52. The proximal end surface 52 may be connected directly to an inner wall 184 of the proximal shaft portion 14 by any suitable method, such as, but not limited to, laser welding.

Referring to FIG. 3, in some implementations, the capped distal tip member 20 defines, in part, the distal end 10b of the delivery apparatus 10. For example, the capped distal tip member 20 may be formed from or an integral part of the core wire 18, or, alternatively, the capped distal tip member 20 may be formed as a separate component, as illustrated, from that of the core wire 18.

The capped distal tip member 20 may define a cup-shaped body 58 having a substantially U-shaped longitudinal section. The cup-shaped body 58 may include a distal, dome-shaped outer axial surface 60 and a proximal, recessed axial surface 62 that corresponds to and may be axially disposed adjacent the rounded, substantially dome-shaped axial/distal end surface 48 of the core wire 18. In some examples, the recessed axial surface 62 is heat-bonded with the axial/distal end surface 48 of the core wire 18. In additional examples, the distal portion of the core wire 18 is melted, with a laser welder or by other suitable means, to form the integral capped distal tip member 20.

The proximal, recessed axial surface 62 of the capped distal tip member 20 may extend axially toward the proximal end 10a of the delivery apparatus 10 to define a substantially annular (in cross-section) axial proximal end surface 64 around the radial outer surface 42 of the core wire 18. The substantially annular axial proximal end surface 64 may extend to an outer radial side surface 66 that extends to the distal, dome-shaped outer axial surface 60. The connection of the substantially annular, axial end surface 64 and the outer radial side surface 66 may define a diameter D2 of the capped distal tip member 20. In some examples, the diameter D2 may be greater than the diameter D1 of core wire 18.

The coil member 22 may be composed of, but is not limited to, a platinum-iridium (Pt/Ir) material in whole or in part. As shown in FIG. 3, the coil member 22 may generally define an inner surface 23 and an outer surface 25. In some examples, the inner surface 23 defines a passage 27 with a diameter that is approximately the same as, but slightly greater than the diameter D1 of core wire 18, to permit the core wire 18 to extend through the passage 27 so that the coil member 22 may be arranged concentrically relative to the core wire 18. Moreover, the coil member 22 may be radiopaque.

Figure 5:
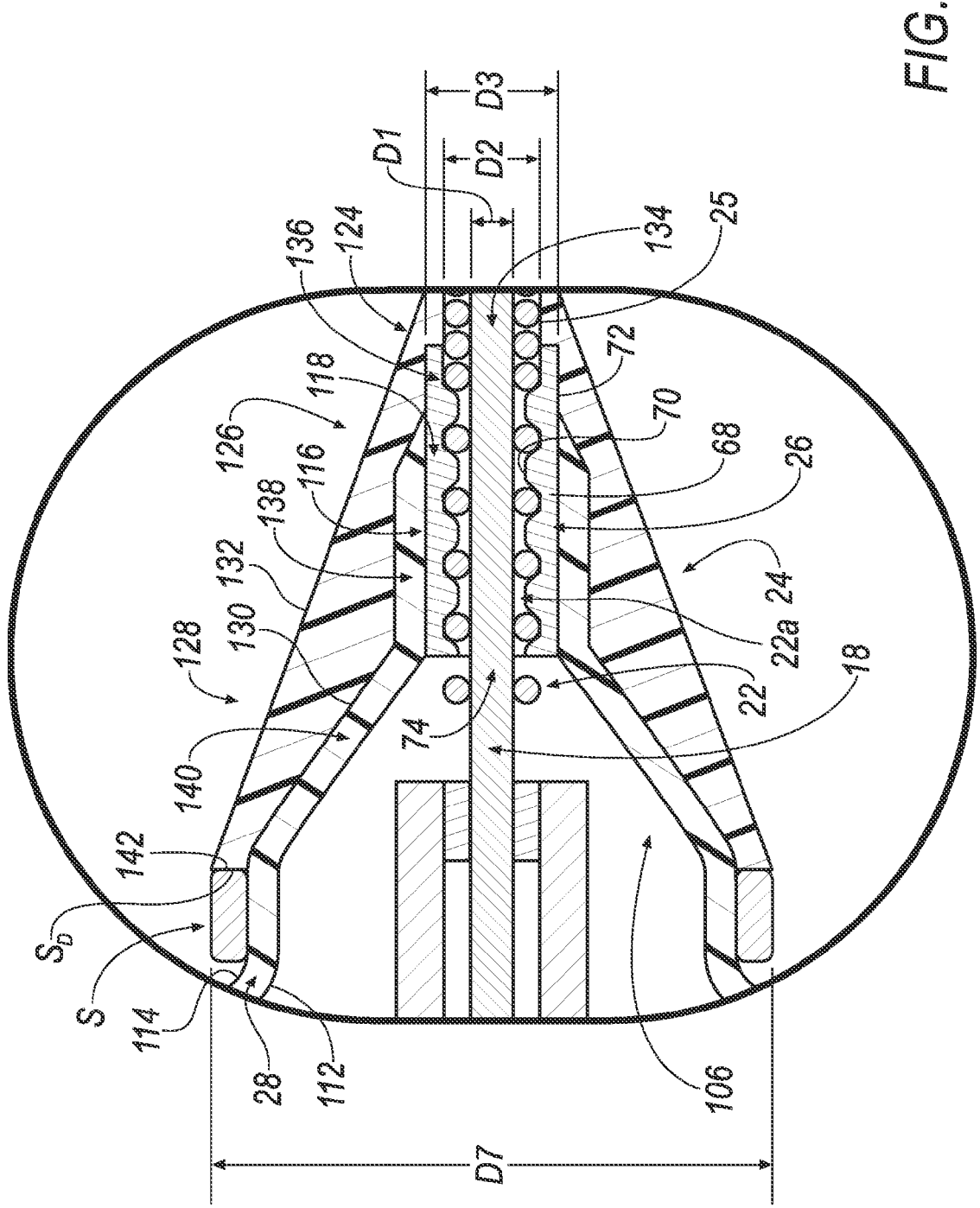
FIG. 5 is an enlarged view of a portion of the distal shaft portion indicated by line 5 of FIG. 2.

The outer surface 25 of the coil member 22 may define the coil member 22 to have an outer diameter substantially equal to or less than the diameter D2 of the capped distal tip member 20. The outer diameter D2 of the coil member 22 may be approximately, but is not limited to, 0.012 inches. In some examples, the coil member 22 has any desirable axial length, for instance, but not limited to, approximately 22 millimeters. As shown in FIG. 5, in some implementations, the proximal portion of the coil member 22 may be stretched to create a series of spaces 22a between individual coils.

Referring back to FIGS. 2 and 3, the coil member 22 may be disposed substantially adjacent to either of or both of the radial outer surface 42 of the core wire 18 and the substantially circular, axial end surface 64 of the capped distal tip member 20. The coil member 22 may be fixedly connected or joined to one or more of the radial outer surface 42 and the substantially annular, axial end surface 64. The coil member 22 may be connected or joined to either or both surfaces 42, 64 via any suitable methodology such as, for example, a laser-welding operation. In some examples, the outer surface 25 of the coil member 22 is heat-bonded with an inner surface 130 of the distal balloon control band 24, shown in FIG. 5. The inner surface 130 of the distal balloon control band 24 may extend into the spaces 22a (not shown).

The cup-shaped body 58 of the capped distal tip member 20 may help to functionally prevent the coil member 22 from axially moving and/or radially separating (i.e., uncoiling) along the core wire 18. Further, the geometry of the rounded, dome-shape surface 60 of the capped distal tip 20 may functionally provide the delivery apparatus 10 with a radiused, atraumatic tip.

Referring to FIG. 5, the distal bonding portion 26 may include, but is not limited to, a substantially cylindrical body, sleeve or tube 68 having an inner radial surface 70 and an outer radial surface 72. The outer radial surface 72 may define a diameter D3. The inner radial surface 70 may define a diameter that may be approximately the same as, but slightly greater than diameter D2 (see e.g., FIG. 3).

The distal bonding portion 26 may include a low-density polyethylene (LDPE) material or the like. In some examples, the distal bonding portion 26 is utilized to bond the coil member 22 with one or more of the balloon 28 and the distal balloon control band 24, which may prevent twisting of the balloon 28 on the core wire 18. Bonding between other components, such as the coil member 22 and the distal balloon control band 24 and the distal bonding portion 26 or other reshaping of the bonding portion 26 may be activated by, for example, treatment of the bonding portion 26 with a laser. The distal bonding portion 26 may extend into the spaces 22a. In some examples, the coil member 22 is stretched to permit the distal bonding portion 26 to extend into the spaces 22a.

The substantially cylindrical tube 68 may be concentrically arranged relative to the core wire 18 and the coil member 22 such that one or more of the core wire 18 and the coil member 22 extends through a passage 74 defined by the inner radial surface 70 of the substantially cylindrical tube 68 of the distal bonding portion 26. The inner radial surface 70 may be disposed adjacent to the outer radial surface 25 of the coil member 22.

Figure 6:
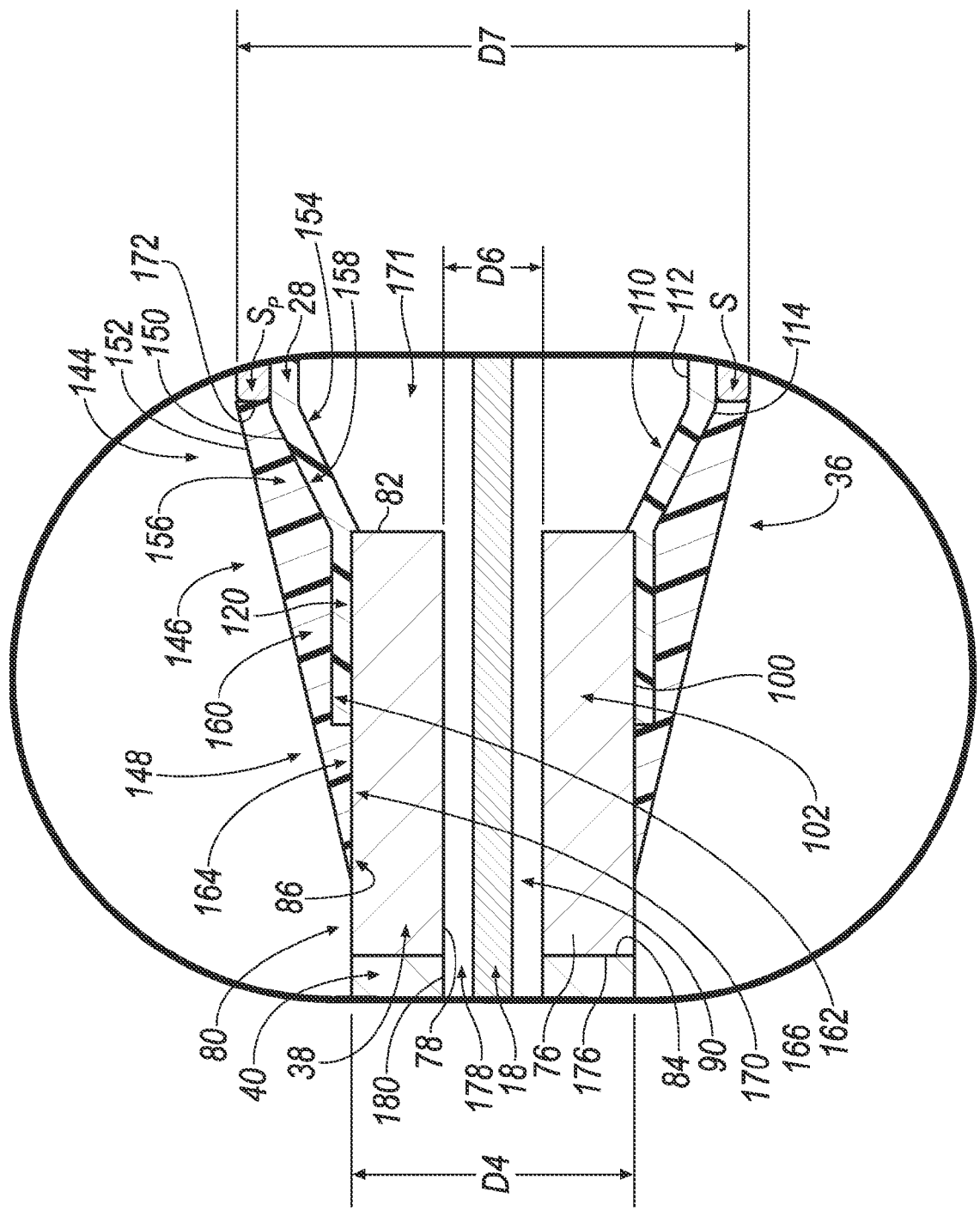
FIG. 6 is an enlarged view of a portion of the distal shaft portion indicated by line 6 of FIG. 2.

Referring to FIG. 6, one or more of the distal shaft mounting portion 38 and the proximal shaft mounting portion 40 may include, but are not limited to, a polymeric material such as a polyamide material. A proximal end of the distal shaft mounting portion 38 may be heat-bonded to a distal end of the proximal shaft mounting portion 40. Although the distal and proximal shaft mounting portions 38, 40 may include a polymeric material in some embodiments, the durometer (i.e., the hardness/softness) of the polymeric material may not necessarily be the same between or within the shaft mounting portions 38, 40. For instance, the hardness/softness of the proximal shaft portion 14, proximal shaft mounting portion 40, and the distal shaft mounting portion 38 can each be selected such that the proximal shaft portion 14 is more rigid than the proximal shaft mounting portion 40 and the distal shaft mounting portion 38, and the proximal shaft mounting portion 40 is more flexible than the proximal shaft portion 14, but less flexible than the distal shaft mounting portion 38. In this configuration, the proximal shaft portion 14 provides rigidity to the apparatus and the proximal shaft mounting portion 40 and the distal shaft mounting portion 38 provide sufficient flexibility to navigate coronary or other vessel anatomy as the distal shaft portion 16 is positioned for deployment.

Figures illustrating the proximal shaft portion 14, the proximal shaft mounting portion 40, the distal shaft mounting portion 38 and the distal shaft portion 16 are not drawn to scale and are merely a convenient representation of those components. The relative lengths of these components can vary as necessary to provide an apparatus that can be used to navigate coronary or other vessel anatomy. For instance, the relative lengths of proximal shaft mounting portion 40 and the distal shaft mounting portion 38 can be approximately 15 centimeters and 35 centimeters, respectively.

As illustrated in FIG. 6, the distal shaft mounting portion 38 may include, but is not limited to, a substantially cylindrical body, sleeve or tube 76 having an inner radial surface 78 and an outer radial surface 80, an axial distal end surface 82 and an axial proximal end surface 84. A passage 90 that may be defined by the inner radial surface 78 may have an inner diameter D6 that extends axially through the distal shaft mounting portion 38 from the axial proximal end surface 84 to the axial distal end surface 82. The distal shaft mounting portion 38 may be concentrically arranged relative to the core wire 18 such that the core wire 18 axially extends through the passage 90.

In some implementations, a proximal portion of the proximal balloon control band 36 is bonded to the outer radial surface 80 of a distal end of the distal shaft mounting portion 38, by any suitable method, such as by laser welding. The area of the outer radial surface covered by the proximal portion of the proximal balloon control band 36, i.e., area 86, may extend part or all of the way over the outer radial surface 80 of distal shaft mounting portion 38. The distal portion of proximal balloon control band 36 may extend radially around the proximal portion of balloon 28. The distal portion of the proximal balloon control band 36 may be made of a material that will stretch as axial chamber 174 as defined by balloon 28 is inflated and snap back or relax into its initial position when axial chamber 174 as defined by balloon 28 is deflated, thereby helping to collapse the balloon 28 and minimize the profile of the apparatus following balloon 28 deflation. In some examples, a proximal bonding portion may secure the proximal balloon control band 36 to the distal end of the distal shaft mounting portion 38 (not shown).

Referring to FIGS. 2 and 5-7, the balloon 28 may include, but is not limited to, for example, a nylon material. The balloon 28 may include a distal segment 106 (see e.g., FIG. 5), an intermediate segment 108 (see e.g., FIG. 7) and a proximal segment 110 (see e.g., FIG. 6) collectively defining an inner surface 112 and an outer surface 114 of the balloon 28.

Referring to FIG. 5, in some implementations, a portion 116 of the inner surface 112 of the distal segment 106 of the balloon 28 may be arranged adjacent to a portion 118 of the outer radial surface 72 of the distal bonding portion 26. Similarly, referring to FIG. 6, in some implementations, a portion 120 of the inner surface 112 of the proximal segment 110 of the balloon 28 may be arranged adjacent to the outer radial surface 80 of the distal shaft mounting portion 38. The inner surface 112 of the portion 120 of the balloon 28 may be bonded to the distal end of distal shaft mounting portion 38, by, for instance, but not limited to laser welding, thereby minimizing the profile of apparatus 10.

With further reference to FIG. 5, the distal balloon control band 24 may include a distal segment 124, an intermediate segment 126 and a proximal segment 128 that collectively define an inner surface 130 and an outer surface 132 of the distal balloon control band 24. In some examples, the outer surface 132 of distal balloon control band 24 generally defines the distal balloon control band 24 to form a conical outer surface tapering in the distal direction.

The distal segment 124 of the distal balloon control band 24 may be arranged concentrically with respect to the core wire 18 and the coil member 22. The inner surface 130 may define the distal balloon control band 24 to include a passage 134 that permits one or more of the core wire 18, the coil member 22, the distal bonding portion 26, and the balloon 28 to axially extend through the distal control band 24.

The passage 134 may include a constant or a non-constant diameter (e.g., creating a tapering, widening, constricting, and/or expanding passage 134) for one or more of the segments 124, 126, and 128. For instance, the passage 134 may decrease in diameter, as shown in FIG. 5, as the distal balloon control band 24 extends from the proximal end 10a toward the distal end 10b of the delivery apparatus 10.

In some examples, one or more of the core wire 18, the coil member 22 and the distal bonding portion 26 axially extend through the passage 134 proximate to one or more of the distal segment 124 and the intermediate segment 126 of the distal balloon control band 24. The inner surface 130 of the distal segment 124 of the distal balloon control band 24 may be disposed substantially adjacent and attached to one or more of the outer surface 25 of the coil member 22 and a portion 136 of the outer surface 72 of the distal bonding portion 26.

The intermediate segment 126 of the distal balloon control band 24 may be arranged concentrically with respect to one or more of the core wire 18, the coil member 22, the distal bonding portion 26 and a portion of the distal segment 106 of the balloon 28. The inner surface 130 of the intermediate segment 126 of the distal balloon control band 24 may be disposed adjacent to a portion 138 of the outer surface 114 of the distal segment 106 of the balloon 28. The portion 138 can be referred to as a distal step portion or a distal tubular portion of the balloon 28.

The proximal segment 128 of the distal balloon control band 24 may be arranged concentrically with respect to one or more of the core wire 18, a portion of the axial length of the coil member 22, and a portion of the distal segment 106 of the balloon 28. The inner surface 130 of the proximal segment 128 of the distal balloon control band 24 may be disposed adjacent to a portion 140 of the outer surface 114 of the distal segment 106 of the balloon 28. The portion 140 may be referred to as a distal ramp portion or distal conical portion of the balloon 28. The distal conical portion 140 may be connected to the distal tubular portion 138 of the balloon 28.

Referring to FIG. 6, the proximal balloon control band 36 may include a distal segment 144, an intermediate segment 146 and a proximal segment 148 collectively defining an inner surface 150 and an outer surface 152. The outer surface 152 of the proximal balloon control band 36 may define the proximal balloon control band to include a proximal outer conical portion, tapering in the proximal direction.

The distal segment 144 of the proximal balloon control band 36 may be arranged concentrically with respect to one or more of the core wire 18 and a portion 154 of the balloon 28. A portion 156 of the inner surface 150 of the proximal balloon control band 36 may be disposed substantially adjacent and attached to a portion 158 of the outer surface 114 of the proximal segment 110 of balloon 28. The portion 158 can be referred to as a proximal ramp portion or the proximal conical portion of the balloon 28.

An intermediate segment 146 of the proximal balloon control band 36 may be arranged concentrically with respect to one or more of the core wire 18, the distal shaft mounting portion 38 and the proximal segment 110 of the balloon 28. A portion 160 of the inner surface 150 of the proximal balloon control band 36 may be disposed adjacent a portion 162 of the outer surface 114 of the proximal segment 110 of the balloon 28. The portion 162 can be referred to as a proximal tubular portion of the balloon 28. The proximal conical portion 158 of the balloon 28 may be connected to the proximal tubular portion 162 of the balloon 28.

The proximal segment 148 of the proximal balloon control band 36 may be arranged concentrically with respect to one or more of the core wire 18, a portion 120 of the balloon 28, and a portion 170 of the distal shaft mounting portion 38. A portion 164 of the inner surface 150 of the proximal balloon control band 36 may be disposed substantially adjacent to the portion 170 of the outer radial surface 80 of the distal shaft mounting portion 38.

The proximal balloon control band 36 may define an axial passage 171 that permits one or more of the core wire 18, the proximal segment 110 of the balloon 28, and the distal shaft mounting portion 38 to axially extend therethrough. Further, the passage 171 may include a constant or non-constant diameter for one or more segments 144, 146, 148 of the proximal balloon control band 36 and/or may increase in diameter as the proximal balloon control band 36 extends from the proximal end 10a toward the distal end 10b of the delivery apparatus 10.

The proximal control bands 36 and distal balloon control bands 24 may apply pressure to the proximal segments 110 and the distal segment 106 of the balloon 28. When fluid F moves into the balloon 28, causing dilation of the balloon 28, the pressure applied by the proximal and distal balloon control bands 36, 24 at the proximal and distal segments 110, 106 of the balloon 28 encourages inflation at the intermediate segment 108 of the balloon 28 first relative to the ends. This improves uniform stent deployment by promoting uncrimping of the stent S at its middle rather than at the distal and proximal ends of the stent S, thereby minimizing over expansion at the ends of the stent S and/or preventing vessel tissue trauma distal and/or proximal to the deployed stent S and area of stenosis. In addition, the pressure applied by the proximal and distal balloon control bands 36, 24 to the proximal and distal segments 110, 106 of the balloon 28 may assist with balloon deflation after stent deployment. As the fluid F is removed from the apparatus 10, the pressure applied by the balloon control bands 36, 24 assists in collapsing the proximal and distal balloon segments 110, 106. This minimizes the profile of the balloon 28 so that it can be removed from the vessel V without snagging the vessel wall or the deployed stent S.

Figure 7:
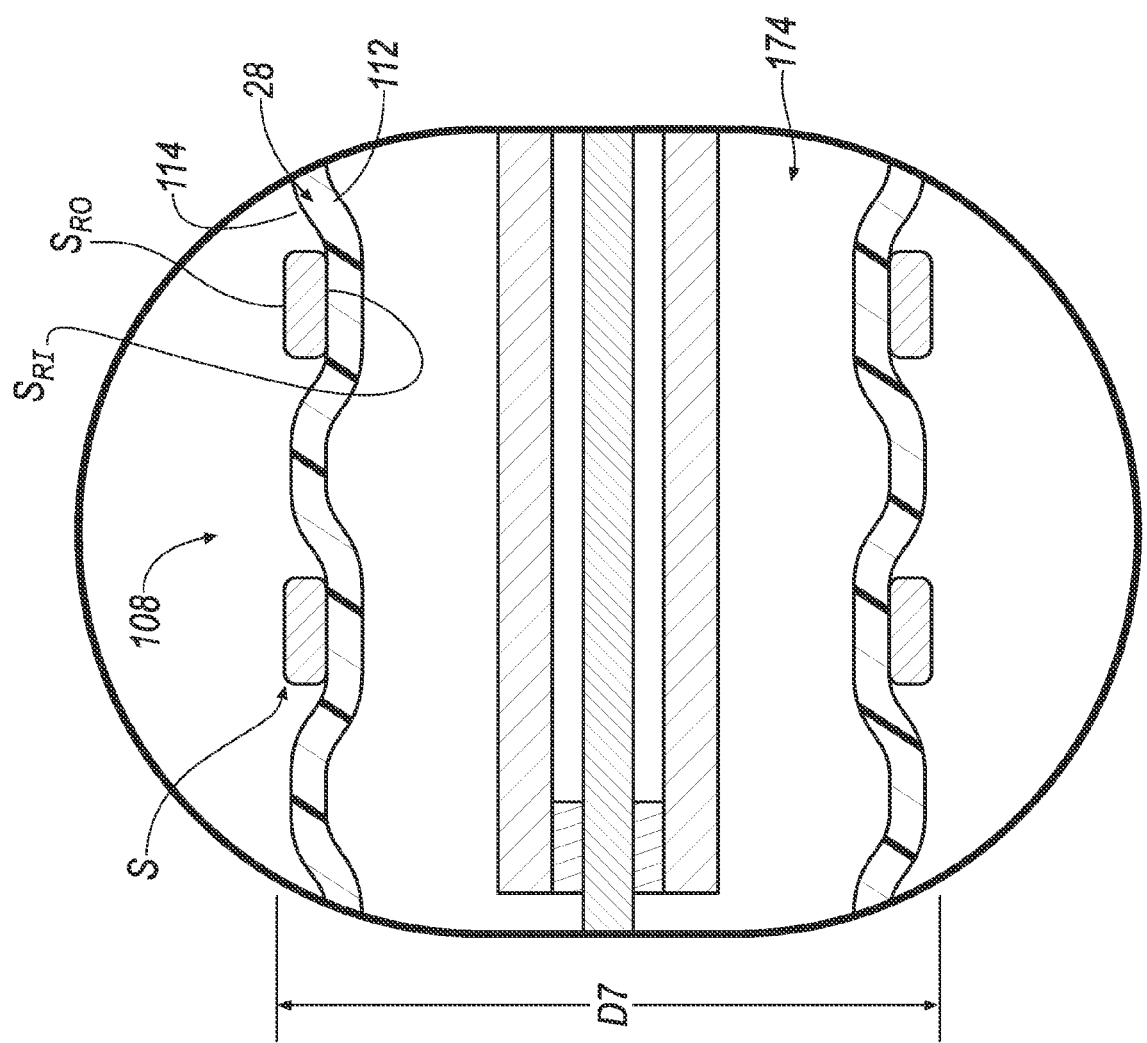
FIG. 7 is an enlarged view of a portion of the distal shaft portion indicated by line 7 of FIG. 2.

FIG. 7 depicts an exemplary intermediate segment 108 of the balloon 28 and a portion of the stent S. In some implementations, the stent S defines an inner radial surface $S_{RI}$ and an outer radial surface $S_{RO}$. The inner radial surface $S_{RI}$ of stent S may be disposed/stowed substantially adjacent to the outer surface 114 of the balloon 28 before/during the axial carrying/delivery of the stent S within the vessel V. In some examples, the inner radial surface $S_{RI}$ of the stent S is crimped onto the outer surface 114 of the balloon 28.

The intermediate segment 108 of the balloon 28 may also be referred to as an intermediate tubular portion of the balloon 28. The outer surface 114 of the intermediate tubular portion 108, taken together with the outer surface $S_{RO}$ of stent S may have a generally constant diameter D7. The intermediate tubular portion 108 may be arranged between and connect the distal and proximal conical portions of the balloon 28.

The balloon 28 may be expanded from a retracted orientation as shown in the figures to an expanded/inflated orientation (not shown). The expansion/inflation of the balloon 28 may be caused by the received fluid F (see e.g., FIG. 1), which may be moved into an axial chamber 174 of the balloon 28 as defined by its inner surface 112. In some examples, the fluid F is prevented from leaking into the vessel V by a seal between the distal and proximal balloon member segments 106, 110 and the distal and proximal balloon control bands 24, 36 and/or the distal bonding portion 26 and the shaft mounting portion 38. Movement of the fluid F into the axial chamber 174 may be permitted by the handle 12 and the proximal shaft portion 14.

When the balloon 28 is expanded/inflated, the outer surface 114 of the balloon 28 imparts a radially, outwardly directed force to the inner radial surface $S_{RI}$ of the stent S, such that the outer diameter D7 of the stent S is increased to a diameter that is greater than the diameter D7 at insertion of the apparatus 10 and the stent S is said to be moved to a deployed orientation. Deployment of the stent S may ultimately result in the outer radial surface $S_{RO}$ of the stent S imparting a radially outwardly directed force to the stenosis $V_S$ of the vessel V.

Upon placing the stent S adjacent to and against the stenosis $V_S$ of the vessel V, the fluid F may be removed from the axial chamber 174 of the balloon 28 such that the outer surface 114 of the balloon 28 is retracted radially away from the stent S and stenosis $V_S$ of the vessel V. When the balloon 28 is moved from the expanded/inflated orientation back to the retracted/non-inflated orientation, the inner radial surface $S_{RI}$ of the stent S may remain in place adjacent to and against the stenosis $V_S$ of the vessel V and be no longer in contact with any portion of the delivery apparatus 10. The distal balloon control band 24 and the proximal balloon control band 36 may include an elastic and/or rigid materials that assist in the forcing of the fluid F out of the balloon 28, such that the balloon 28 may be collapsed/retracted to its non-inflated orientation.

Referring now to FIGS. 2 and 6, the second axial/proximal end 84 of the distal shaft mounting portion 38 may be disposed adjacent to and connected/joined to a first axial/distal end 176 of the proximal shaft mounting portion 40. As shown in FIG. 6, the core wire 18 may extend toward the proximal end 10a of the delivery apparatus 10, through the passage 90 of the distal shaft mounting portion 38 and into a passage 178 that may be defined a first inner radial surface 180 of the proximal shaft mounting portion 40. The passage 178 may define an inner diameter that is approximately equal to the diameter D6.

Referring to FIG. 2 and the expanded view in FIG. 4, the core wire 18 may extend further toward the proximal end 10a of the delivery apparatus 10 and through the passage 178 such that the second, axial proximal end segment 46 of the core wire 18 may be disposed within or proximate to a passage 182 of the distal end 14b of the proximal shaft portion 14. The length of passage 182 containing the core wire 18, i.e., the passage 202, may be any suitable distance, allowing for improved attachment and reduced kinking (where proximal shaft portion 14 comprises a catheter) of the proximal shaft portion 14 near the site of attachment to the distal shaft portion 16. In some embodiments, the passage 182 may be defined by an inner surface 184 of the proximal shaft portion 14.

One or more of the second axial end segment 46 of the core wire 18 and an axial/proximal end surface 186 of the proximal shaft mounting portion 40 permits the distal shaft portion 16 to be connected to the proximal shaft portion 14. In some examples, one or more of the axial/proximal end surface 186 of the proximal shaft mounting portion 40 may be disposed adjacent and connected/joined to a first axial/distal end surface 188 of the proximal shaft portion 14.

A second inner radial surface 190 of the proximal shaft mounting portion 40 may define an inner diameter, D8. In some examples, an outer radial surface 192 of the proximal shaft portion 14 may include a diameter that is approximately the same as but less than the diameter D8. The second inner radial surface 190 of the proximal shaft mounting portion 40 may be disposed adjacent to and connected/joined to the outer radial surface 192 of the proximal shaft portion 14.

Referring to FIG. 4, a portion of the core wire 18 near the proximal end 52 can be connected to the inner surface 184 of the proximal shaft portion 14, by any suitable method, such as, for example, laser welding.

Figure 8:
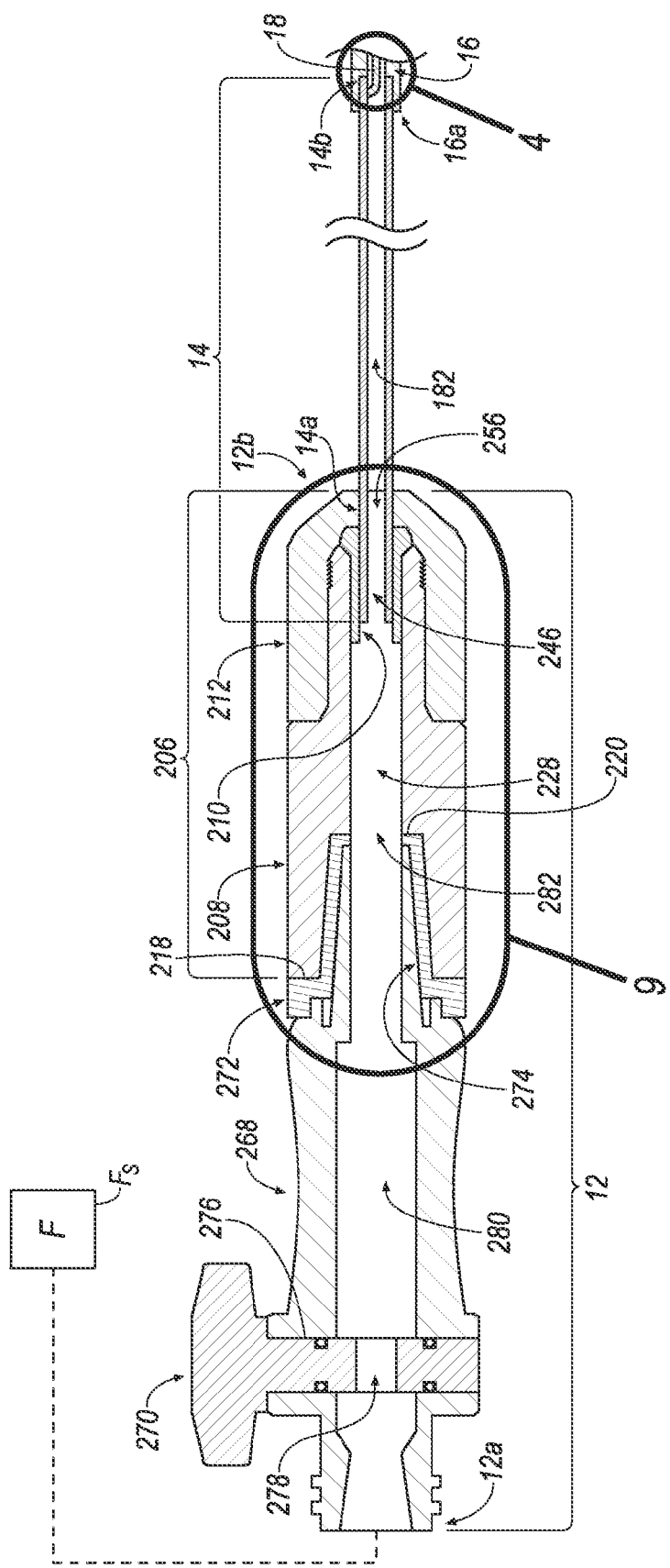
FIG. 8 is a longitudinal-sectional view of an exemplary handle portion of the balloon catheter delivery apparatus, wherein the handle portion includes an optional stop cock.

FIG. 8 depicts an exemplary arrangement of the handle 12, the proximal shaft portion 14 and the proximal end 16a of the distal shaft portion 16. In some implementations, the proximal shaft portion 14 is ultra-violet (UV) adhesive-bonded to the handle 12.

Figure 9:
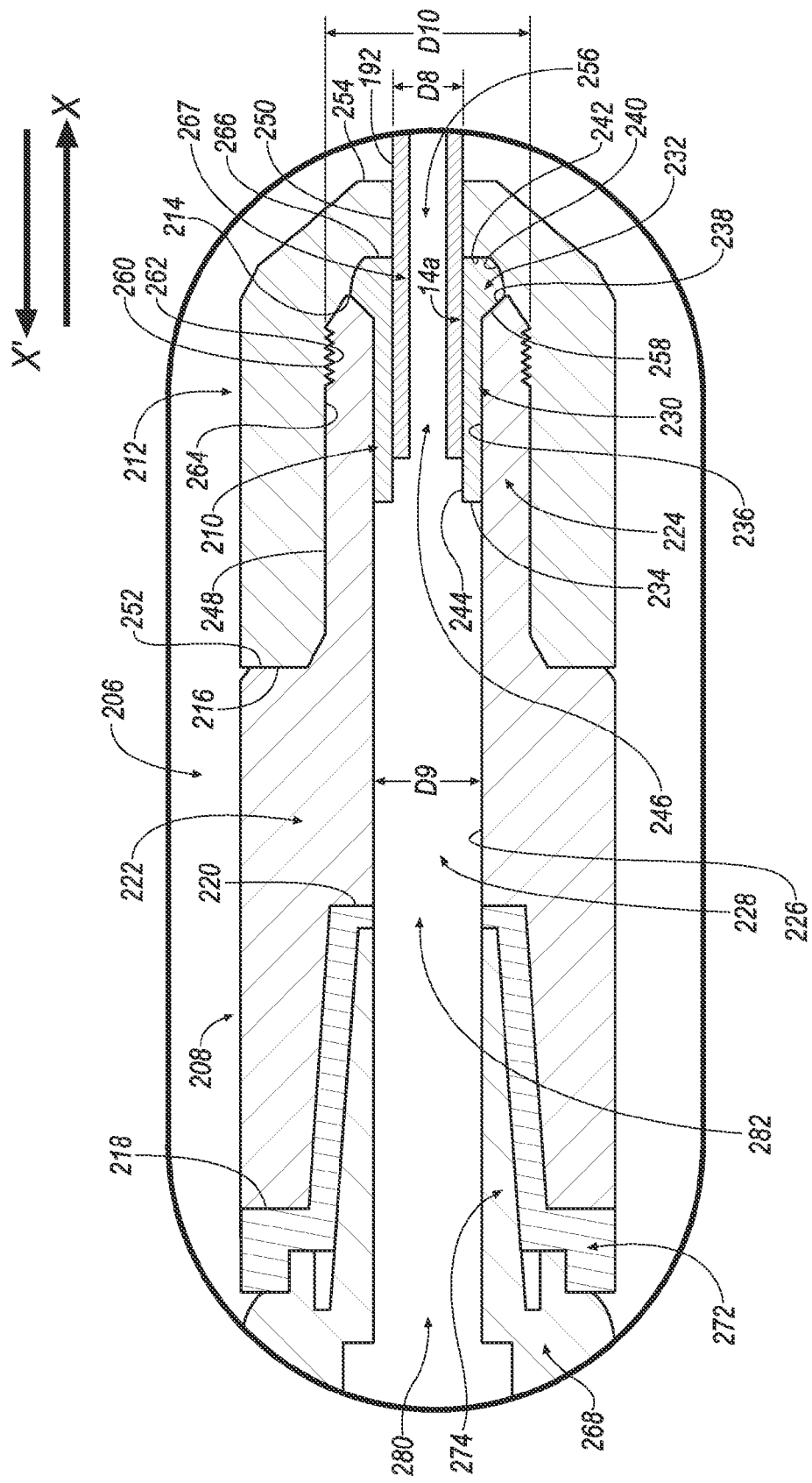
FIG. 9 is an enlarged view of a portion of the handle portion indicated by line 10 of FIG. 8.
Figure 10:
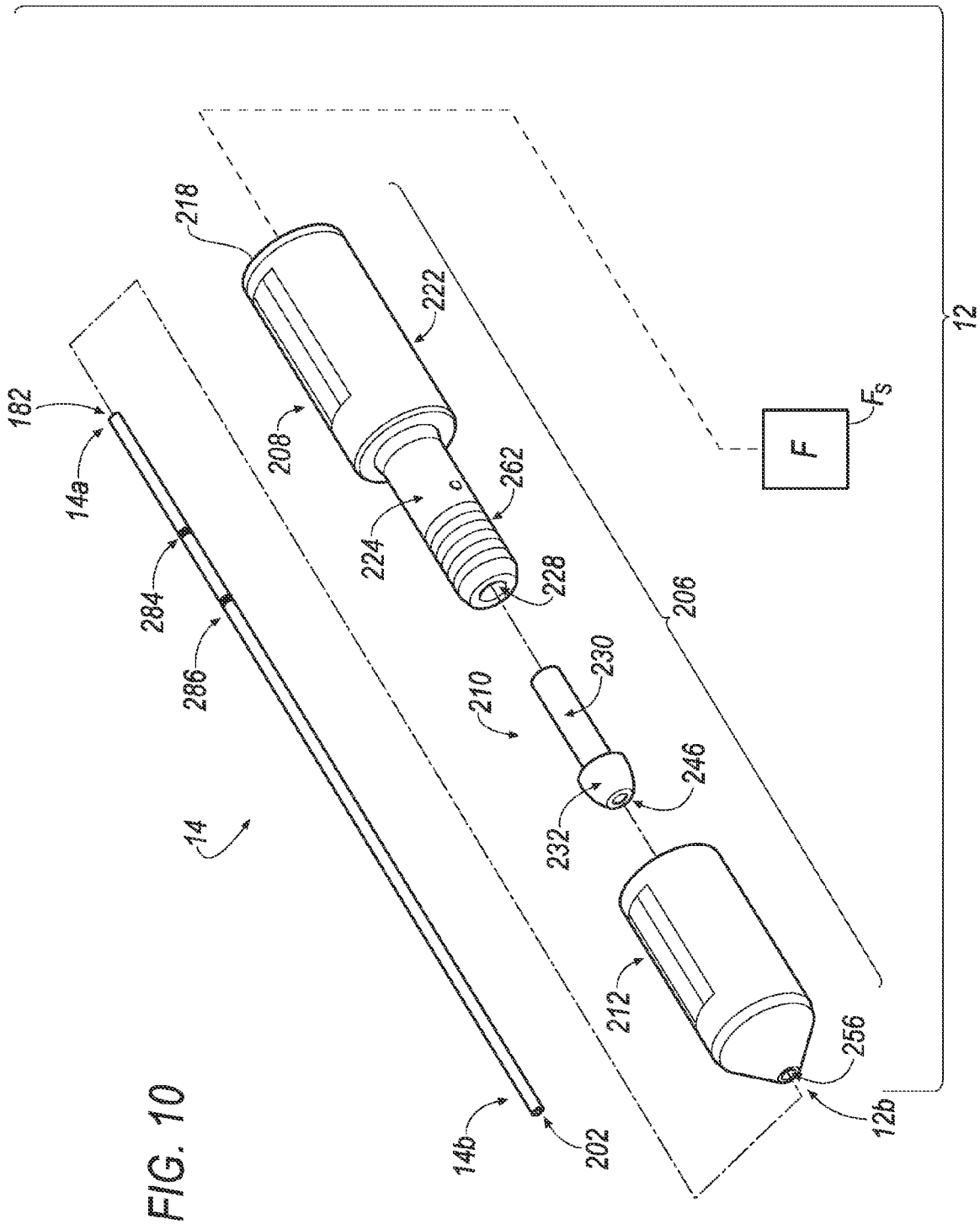
FIG. 10 is a perspective view of an exemplary handle portion and a proximal shaft portion of the balloon catheter apparatus of FIG. 1.

As seen in FIGS. 8-10, the handle 12 may include a docking torque apparatus 206, which may include a base portion 208, a collet portion 210, and a head portion 212. The base portion 208 and the head portion 212 may include an acrylonitrile butadiene styrene (ABS) material. The collet portion 210 may include a brass material. In some examples, where the handle comprises two pieces, the collet portion 210 and the cylindrical socket portion 224 are integral, i.e., combined to form a unitary piece.

Referring to FIG. 9, the base portion 208 may include a first axial/distal end 214, a second axial/distal end 216, a first axial/proximal end 218 and a second axial/proximal end 220. The base portion 208 may include a substantially cylindrical sleeve portion 222 and a substantially cylindrical socket portion 224. The substantially cylindrical sleeve portion 222 may be integrally formed with the substantially cylindrical socket portion 224.

The substantially cylindrical sleeve portion 222 may extend axially from the first axial/proximal end 218 to the second axial/distal end 216. The substantially cylindrical socket portion 224 may extend axially from the second axial/distal end 216 to the first axial/distal end 214.

The base portion 208 may include an inner radial surface 226 that may define an axial passage 228 with an internal diameter D9. The collet portion 210 may include a substantially tubular sleeve portion 230 connected to a chuck portion 232. The substantially tubular sleeve portion 230 may define the collet portion 210 to include a first proximal end surface 234 connected to a first outer radial surface 236 that is connected to a second proximal end surface 238 of the chuck portion 232. The second proximal end surface 238 of the chuck portion 232 may be connected to a second outer radial surface 240 of the chuck portion 232 that is connected to a distal end surface 242 of the chuck portion 232. The substantially tubular sleeve portion 230 and the chuck portion 232 may define an inner radial surface 244 that defines an axial passage 246 that extends axially from the first proximal end surface 234 to the distal end surface 242.

The first outer radial surface 236 of the collet portion 210 may include a diameter approximately equal to but less than the diameter D9 of the axial passage 228 of the base portion 208. The axial passage 246 of the collet portion 210 may include an inner diameter that may be approximately equal to but slightly greater than the outer diameter D8 of the proximal shaft portion 14.

The head portion 212 may include a U-shaped cross-section having a first inner radial surface 248, a second inner radial surface 250, an axial/proximal surface 252 and an axial/distal surface 254. The first inner radial surface 248 may include a diameter D10 that may be approximately similar to, but slightly greater than, an outer diameter of the substantially cylindrical socket portion 224 of the base portion 208. The second inner radial surface 250 may define the head portion 212 to include a passage 256 that is approximately the same as, but slightly greater than, the outer diameter D8 of the proximal shaft portion 14.

The substantially tubular sleeve portion 230 of the collet portion 210 may be axially disposed within the axial passage 228 of the substantially cylindrical socket portion 224 such that the second proximal end surface 238 of the chuck portion 232 may be arranged substantially adjacent/proximate/opposingly facing a chamfered/conical surface 258 of the first axial/distal end 214 of the substantially cylindrical socket portion 224.

The first inner radial surface 248 of the head portion 212 may include a threaded surface 260 that connectably interfaces with a correspondingly-threaded surface 262 formed on an outer radial surface 264 of the substantially cylindrical socket portion 224. The threaded connected of the head portion 212 and the substantially cylindrical socket portion 224 of the base portion 208 permits the head portion 212 to be axially movable according to the direction of arrows, X (i.e., axially toward the distal end 10b), X' (axially toward the proximal end 10a), relative one or more of the base portion 208, collet portion 210 and the proximal end 14a of the proximal shaft portion 14.

As seen in FIG. 9, the proximal shaft portion 14 may be axially inserted through the passage 256 of the head portion 212 and into the axial passage 246 of the collet portion 210. As such, upon axially moving the head portion 212 according to the direction of the arrow, X', an axial/proximal surface 266 of the head portion 212 may come into contact with the distal end surface 242 of the chuck portion 232 such that the second proximal end surface 238 of the chuck portion 232 may come into contact with the chamfered/conical surface 258 of the first axial/distal end 214 of the substantially cylindrical socket portion 224.

As the second proximal end surface 238 comes into contact with the chamfered/conical surface 258, the axial passage 246 of the collet portion 210 at least proximate to the chuck portion 232 may be radially reduced such that the inner radial surface 244, at least proximate to the chuck portion 232, may engage, grip, /or "bite into" a portion 267 of the outer radial surface 192 proximate to at least the proximal end 14a of the proximal shaft portion 14. The engagement of the chuck portion 232 and the proximal end 14a of the proximal shaft portion 14 may provide a frictional, axially-selective connection of the handle 12 and the proximal shaft portion 14.

Referring to FIGS. 8-10, the handle 12 may also include a handle body 268, an optional stopcock 270, and a strain relief member 272. The handle body 268 may axially extend from the proximal end 10a toward the distal end 10b of the delivery apparatus 10 to define a nose portion 274 that is press-fitted to the strain relief member 272. The strain relief member 272 may be axially connected to one or more of the first axial/proximal end 218 and the second axial/proximal end 220 of the base portion 208.

The optional stopcock 270 may be inserted through a radial passage 276 formed in the handle body 268. In some examples, the optional stopcock 270 may be press-fitted to the handle body 268 such that the stopcock 270 may be rotatably connected to the handle body 268 (e.g., to permit the stopcock 270 to be able to turn 90° in a "quarter-turn" orientation relative to the handle body 268 and within the radial passage 276). The optionally integrated stopcock may effectuate a time savings because the user will not have to assemble the stopcock as an additional part with the delivery apparatus 10.

The stopcock 270 may include an axially-alignable passage 278. Rotation of the stopcock 270 permit the stopcock to act as a valve member to permit or deny movement of the fluid, F, through the handle body 268.

The stopcock 270 may be rotatably-connected to the handle body 268 such that the axial passage 278 of the stopcock 270 may be axially aligned with an axial passage 280 extending through the handle body 268 and an axial passage 282 extending through the strain relief member 272. Accordingly, as seen in FIG. 8, the axial passage 278 may be axially aligned with the axial passages 280, 282 of the handle body 268 and the strain relief member 272. The fluid F may be provided through the axial passages 228, 246, 256, 278, 280, 282 of the handle 12, through the axial passages 182, 202 of the proximal shaft portion 14 and through the axial passages 90, 178 (see, e.g., FIGS. 4 and 6) of the distal shaft portion 12 and into the axial chamber 174 of the balloon 28. The passages 90, 178, 182, 202, 228, 246, 256, 278, 280 and 282 may be in fluid communication with one another and axial chamber 174 in order to permit the fluid F to be moved into the balloon 28 in order to permit the balloon 28 to be moved to an inflated orientation and deploy the stent S.

In some implementations, the handle body 268 does not include the stopcock 270. A valve may be located upstream of the handle body 268 to control flow into the axial passage 280 of the handle body 268.

Referring to FIGS. 1 and 10, the proximal shaft portion 14 may include a stainless steel material and the outer radial surface 192 of the proximal shaft portion may be coated with a polytetrafluoroethylene (PTFE) material. The outer radial surface 192 may include a proximal depth marker 284 and a distal depth marker 286 formed on outer radial surface 192 of the proximal shaft portion 14. The proximal depth marker 284 may be arranged on the outer radial surface 192 approximately 100 centimeters from the distal end 10b of the delivery apparatus 10. The distal depth marker 286 may be arranged on the outer radial surface 192 approximately 90 centimeters from the distal end 10b of the delivery apparatus 10.

Referring to FIGS. 2, 5 and 7, the proximal marker band 32 and the distal marker band 34 may be formed on the radial outer surface 42 of the core wire 18. The proximal marker band 32 permits a user to gauge the approximate axial location of where the proximal segment 110 and intermediate segment 108 of the balloon 28 are joined together. The distal marker band 34 permits the user to know of an approximate axial location of where the distal segment 106 and intermediate segment 108 of the balloon 28 are joined together. As such, by knowing the location of the segments 106-110 of the balloon 28, the user may also know the approximate axial location of the stent S as well.

Each of the proximal and distal marker bands 32, 34 may include an inner radial surface 288 and an outer radial surface 290. The inner radial surface 288 may be connectively swaged to the radial outer surface 42 of the core wire 18. The proximal and distal marker bands 32, 34 may include any desirable material, such as, for example, a platinum-iridium material.

Referring to FIGS. 1 and 2, one or more protective tubular members 292 may be arranged coaxially relative to the core wire 18 and the proximal and distal marker bands 32, 34.

The protective tubular member 292 may include an inner radial surface 294 and an outer radial surface 296. The outer radial surface 296 may define an outer diameter D11. The inner radial surface 294 may be arranged adjacent to the outer radial surface 290 of the proximal and distal marker bands 30, 32. The protective tubular member 292 may include any desirable material, such as a polymer. An example of a polymer material includes, without limitation, a polyamide material.

The protective tubular member 292 may prevent the inner surface 112 of the balloon 28 from contacting the outer radial surface 290 of the proximal and distal marker bands 32, 34. By preventing the inner surface 112 of the balloon 28 from contacting the outer radial surface 290 of the proximal and distal marker bands 32, 34, any axial shifting of the proximal and distal marker bands 32, 34 relative the core wire 18 may be reduced/eliminated as the delivery apparatus 10 is being inserted into the vessel, V. In addition, the protective tubular member 292 may prevent the stent from being compressed to a diameter so small that it cannot be properly deployed.

In some implementations, the distal shaft portion 16 of the delivery apparatus 10 may be coated with a friction-reducing material that may assist a user in the inserting or removing the delivery apparatus 10. The coating may include a hydrophillic coating, which may include a polymer-based material. Not every element 18-40 of the distal shaft portion 16 may be coated with the friction-reducing material. For example, the balloon 28 may not be coated with the friction-reducing material. Further, although the stent S may not necessarily be considered to be part of the delivery apparatus 10, the stent S may also not be coated with the friction-reducing material.

A protective polytetrafluoroethylene (PTFE) tubular sheath (not shown) may be arranged about the outer radial surface $S_{RO}$ of the stent S or the catheter tubing. The sheath may be provided with the delivery apparatus 10 if, for example, the stent S is arranged relative to the delivery apparatus in a "pre-mounted" configuration. Accordingly, prior to utilizing the delivery apparatus 10, a user may remove the sheath in order to expose the stent S.

In some implementations, the axial core wire 18 may include a stainless steel material. Moreover, the distal balloon control band 24 may include a polyurethane material and the handle body 268 may include a polycarbonate (PC) material. The stopcock 270 may include an acetal material. The strain relief member 272 may include a thermoplastic polyether material, a polybutylene material, a terphthalate material, a polyether glycol material or the like.

One or more of the structures of the shaft portions 18-40, may include a material that lends itself to having a non-rigid, shapeable quality. Further, one or more of the structures 18-40 may include a material that lends itself to having similar or dissimilar durometers (i.e., softness/hardness ratings). Further, although the distal shaft portion 16 is described to include structures identified at 18-40, the distal shaft portion 16 is not limited to the number of, type or geometry of structure identified at 18-40 and that the invention may be practiced with any desirable number of, type or geometry of structure.

The balloon 28 may be folded upon itself one or more times. Accordingly, although the balloon 28 is illustrated in FIGS. 1, 2, 5, 6, and 7 to include one, non-folded layer, the illustration of the balloon 28 in the figures does not limit the disclosed structure or function of the invention. Various balloon folding, combinable with this disclosure, can be found in U.S. Pat. No. 6,071,285 and U.S. Pat. No. 6,120,533, which are hereby incorporated by reference in their entireties.

Referring to FIGS. 11 and 12, the distal shaft portion 16 is shown prior to inflation. FIGS. 11 and 12 also illustrate a "folded balloon" in which the balloon is folded upon itself. Although, for simplicity, the balloon is shown as being folded on itself three times, the balloon can be folded in any manner.

In some implementations, the balloon delivery apparatus includes a catheter comprising a proximal hypotube portion, a distal flexible tube portion, and a lumen disposed longitudinally through the proximal hypotube portion and distal flexible tube portion. The balloon delivery apparatus also includes a balloon having a proximal end that is affixed to a distal shaft mounting portion of the proximal hypotube portion and a distal end that is affixed to a core wire at a location proximal to the distal tip of the core wire. The balloon can be coaxial with the core wire and in fluid communication with the lumen of the proximal hypotube portion and the distal flexible tube portion. The balloon delivery apparatus includes a plurality of balloon control bands, wherein at least one balloon control band is located at the proximal end of the balloon and at least one balloon control band is located at the distal end of the balloon. The balloon control bands may restrict the balloon's longitudinal expansion upon inflation.

In some examples, the proximal hypotube portion comprises a first material and the distal flexible tube section comprises a second material. For example, the proximal hypotube portion comprises a metal. In additional examples, the proximal hypotube portion comprises stainless steel. And in some instances, the stainless steel is coated with PTFE. The proximal hypotube section may further include a plurality of optical markers (e.g., depth markers). The distal flexible tube portion may comprise a polymer material, which may comprise a silicone rubber material.

In some implementations, the distal tip of the core wire further comprises a prolate spherical or hemispherical cap. The core wire further comprises a coiled section wherein the coiled section is located proximal to the distal tip. The core wire may include a plurality of depth markers, wherein at least one depth marker is located approximately concentrically with the proximal end of the balloon and at least one depth marker is located approximately concentrically with the distal end of the balloon. Optionally, the core wire includes at least one protective tubular member having a length approximately equal to the length of the balloon, wherein the protective tubular member is coaxial with the core wire and the balloon. For example, the protective tubular member can be disposed between the depth marker located approximately concentrically with the proximal end of the balloon and the depth marker can be located approximately concentrically with the distal end of the balloon. In some examples, the balloon control bands comprise an elastomer material that elastically expands upon inflation of the balloon.

In some implementations, the balloon is a non-compliant balloon comprising a polymer material. For instance, the balloon comprises a polyamide polymer material.

In some examples, the apparatus includes a handle affixed to the proximal hypotube portion. The handle may include an inflation control that controls the inflation of the balloon.

In some implementations, the balloon delivery catheter apparatus includes a catheter comprising a proximal hypotube, a distal flexible tube, and a lumen that extends longitudinally throughout both tubes. The balloon delivery catheter apparatus also includes a balloon near the distal end of the proximal hypotube that fluidly communicates with the lumen. The balloon includes a distal end, a proximal end, and an intermediate segment. A core wire extending throughout at least a portion of the catheter lumen and beyond the distal end of the balloon includes a proximal end, a distal tip, and a coiled member. The coiled member can be disposed between the proximal end and the distal tip. A proximal balloon control band may be concentrically arranged around the proximal end of the balloon, and a distal balloon control band may be concentrically arranged about the distal end of the balloon. The distal and proximal balloon control bands may restrict inflation of the balloon at the proximal and distal ends of the balloon. The distal and proximal balloon control bands may comprise an elastomer material that elastically expands during inflation of the balloon and contracts upon deflation.

In some examples, a bonding element coaxially mounted about the coiled member of the core wire secures the distal end of the balloon to the coil member.

A portion of the distal balloon control band may be affixed to the distal end of the balloon. The proximal end of the balloon can be affixed to the distal end the proximal hypotube, and the proximal balloon control band can be affixed to the proximal hypotube. Or, the proximal balloon control band can be affixed to the proximal end of the balloon. In additional examples, the proximal end of the core wire is affixed to the distal end of the proximal hypotube.

In some examples, a plurality of depth markers are affixed to the catheter (e.g., affixed to the proximal hypotube). Moreover, at least one depth marker may be approximately concentric with the proximal end of the balloon and at least one depth marker may be approximately concentric with the distal end of the balloon.

A protective tubing member, having a proximal end and a distal end, may be affixed to the core wire so that the proximal end of the member is approximately concentric with the proximal end of the balloon, and the distal end of the member is approximately concentric with the distal end of the balloon.

In some implementations, the distal tip comprises a round surface comprising a hemisphere or prolate hemisphere. The balloon may comprise a polyamide polymer material (e.g., a polyamide material (e.g., Nylon)).

The proximal hypotube may comprise a first material and the distal flexible tube may comprise a second material. For example, the proximal hypotube may comprise stainless steel. In some instances, the stainless steel is substantially coated with a polymer material comprising PTFE. Moreover, the distal flexible tube may comprise a polymer material comprising silicone rubber.

Upon inflation, the balloon may adopt a geometry having two inward facing cones and a cylindrical segment located between said cones.

In some implementations, a handle may be connected to and in fluid communication with the lumen of the proximal hypotube. The handle may include a docking torque apparatus having a base portion, a collet portion disposed within a passage of the base portion 208, and a head portion movably connected to the base portion. The head portion may be selectively engagable with the collet portion. The proximal shaft section of the hypotube may be disposable through one or more of the head portion, the collet portion, or the base portion. In some examples, the handle includes a strain relief member connected to the handle body and/or the base portion.

A method of treating vascular stenosis in a patient may include providing a balloon delivery apparatus that includes a handle having a handle body, a catheter having a hypotube section, a distal shaft section, and a lumen extending longitudinally throughout both sections. The hypotube section may be connected to the handle body, and the handle body may be in fluid communication with the lumen. The balloon delivery apparatus includes a balloon having a distal segment, an intermediate segment, and a proximal segment, each of which is defined by an inner surface and an outer surface. The proximal segment of the balloon may be affixed to the distal end of the hypotube section and in fluid communication with the lumen of the hypotube section. The balloon delivery apparatus includes a distal balloon control band having an inner surface, an outer surface, and a proximal end surface and a proximal balloon control band having an inner surface, an outer surface and a distal end surface. The inner surface of the distal balloon control band is adjacent to the outer surface of the distal segment of the balloon. The inner surface of the proximal balloon control band is adjacent to the outer surface of the proximal segment of the balloon member. A core wire extends through a portion of the distal shaft section and entirely through the balloon. The handle slidably engages the hypotube section of the catheter, and rotational movement of the handle longitudinally advances or retracts the core wire, the hypotubes section, the distal shaft section, or any combination thereof. Several methods further comprise inserting the balloon into a blood vessel of a patient. And some methods comprise advancing the balloon sufficiently into the vessel such that a portion of the intermediate segment of the balloon is approximately concentric with the stenosis. Some methods further comprise inflating the balloon such that the stenosis is at least partially alleviated. And, some methods further comprise deflating the balloon member and removing the balloon from the patient.

A number of implementations have been described. Nevertheless, it will be understood that various modifications may be made without departing from the spirit and scope of the disclosure. Accordingly, other implementations are within the scope of the following claims.

What is claimed is:

1. A balloon delivery catheter apparatus comprising:
a catheter tubing defining a lumen therethrough;
a balloon disposed near a distal end of the catheter tubing and moving between deflated and inflated states;
a core wire having a proximal end attached to the catheter tubing inside the lumen and extending distally away and substantially co-axially with the catheter tubing through the balloon to a distal free end;
proximal and distal balloon control bands concentrically arranged around respective proximal and distal end portions of the balloon, each balloon control band comprising an elastic material that expands during inflation of the balloon and contracts upon deflation of the balloon, the balloon control bands impeding expansion of the proximal and distal end portions of the balloon and assisting deflation of the balloon after balloon inflation;
a coil disposed around the core wire, the coil having a proximal end attached to at least one of the distal end portion of the balloon and the distal balloon control band; and
a balloon support tube co-axially disposed over the core wire and within the balloon, wherein the balloon support tube prevents compression of the balloon below a threshold diameter; and
a laser activated low density polyethylene bonding portion abutting and interposed between the coil and each of the distal end portion of the balloon and the distal balloon control band, the laser activated low density polyethylene bonding the coil and one or more of the balloon and the distal balloon control band, the laser activated low density polyethylene bonding portion having a first state before laser activation and a second state after activation, wherein the laser activated low density polyethylene bonding portion is unbonded to the coil in the first state and the laser activated low density polyethylene bonding portion is bonded to the coil and extending into spaces defined by the coil in the second state;
wherein the control bands each have a diametric cross-section larger than the balloon in its uninflated state and an unexpanded stent received over the balloon to impede axial movement of the unexpanded stent off of the balloon.

2. The balloon delivery catheter apparatus of claim 1, wherein the proximal and distal balloon control bands are secured to the respective proximal and distal end portions of the balloon.

3. The balloon delivery catheter apparatus of claim 1, wherein the proximal end portion of the balloon and the proximal balloon control band are both attached to the catheter tubing.

4. The balloon delivery catheter apparatus of claim 3, wherein the proximal balloon control band is attached at least partially to the balloon and at least partially to the catheter tubing.

5. The balloon delivery catheter apparatus of claim 1, wherein the distal balloon control band is attached at least partially to the balloon and at least partially to the core wire.

6. The balloon delivery catheter apparatus of claim 1, wherein each balloon control band has a non-uniform cross-sectional thickness along an axial direction of the balloon control band.

7. The balloon delivery catheter apparatus of claim 6, wherein each balloon control band has first and second end portions, the first end portion having a larger diametric cross-section than the second end portion, the first end portion of each balloon control band disposed adjacent to a received stent on the balloon.

8. The balloon delivery catheter apparatus of claim 1, wherein the balloon and the balloon control bands are coaxially disposed about the core wire.

9. The balloon delivery catheter apparatus of claim 1, wherein the coil extends beyond the distal end portion of the balloon.

10. The balloon delivery catheter apparatus of claim 1, wherein the balloon control bands restrict expansion of at least the end portions of the balloon to a threshold diameter.

11. The balloon delivery catheter apparatus of claim 1, further comprising a handle received by a proximal end of the catheter tubing, the handle comprising:
a handle base defining a handle lumen therethrough;
a collet received at least partially in the handle lumen at a distal end portion of the handle base, the collet defining a collet lumen therethrough; and
a handle head releasably connected to the distal end portion of the handle base over the collet, the handle head defining an aperture axially aligned with the collet lumen and sized to receive the proximal end of the catheter tubing therethrough and at least partially in the collet lumen;
wherein the handle lumen is in fluid communication with the lumen of the received catheter tubing; and
wherein movement of the handle head toward the handle base causes constriction of the collet about the received catheter tubing.

12. The balloon delivery catheter apparatus of claim 11, wherein the collet comprises:
a substantially tubular section having an outer diameter less than or equal to a diameter of the handle lumen; and
a chuck attached to the substantially tubular section and having an outer diameter larger than the handle lumen, the chuck defining a chamfered surface arranged to engage an opposing chamfered surface of the handle base;
wherein movement of the handle head toward the handle base causes movement of the collet toward the handle base and the chamfered surface of the handle base to exert a substantially radially inward force on the opposing chamfered surface of the chuck.

13. The balloon delivery catheter apparatus of claim 11, wherein the handle head is threadably received by the distal end portion of the handle base.

14. The balloon delivery catheter apparatus of claim 11, wherein the handle further comprises a valve member disposed on a proximal end portion of the handle base.

15. The balloon delivery catheter apparatus of claim 11, wherein the handle further comprises a strain relief disposed on at least one of the handle base and the handle head.

16. A balloon delivery catheter apparatus comprising:
a catheter tubing defining a lumen therethrough;
a balloon disposed near a distal end of the catheter tubing and moving between deflated and inflated states;
a core wire having a proximal end attached near the distal end of the catheter tubing inside the lumen and extending distally away and substantially co-axially with the catheter tubing through the balloon to a distal free end;
a coil disposed around the core wire, the coil having a proximal end attached to at least one of the distal end portion of the balloon and the distal balloon control band;
a balloon support tube co-axially disposed over the core wire and within the balloon; and
a laser activated low density polyethylene bonding portion abutting and interposed between the coil and the distal end portion of the balloon, the laser activated low density polyethylene bonding portion having a first state before laser activation and a second state after activation, wherein the laser activated low density polyethylene bonding portion is unbonded to the coil in the first state and the laser activated low density polyethylene bonding portion is bonded to the coil and extending into spaces defined by the coil in the second state; wherein the balloon support tube prevents compression of the balloon below a threshold diameter.

17. The balloon delivery catheter apparatus of claim 16, wherein the balloon support tube prevents compression of a received stent over the balloon to a diameter less than a threshold un-deployed stent diameter.

18. The balloon delivery catheter apparatus of claim 16, wherein the balloon support tube has an axial length less than or equal to an axial length of the balloon.

19. The balloon delivery catheter apparatus of claim 16, wherein the balloon support tube is attached to the core wire so that a proximal end of the balloon support tube is approximately concentric with a proximal end of the balloon, and a distal end of the balloon support tube is approximately concentric with a distal end of the balloon.

20. The balloon delivery catheter apparatus of claim 16, wherein the balloon support tube comprises a polyamide material.

21. The balloon delivery catheter apparatus of claim 16, further comprising proximal and distal marker bands disposed on the core wire near respective proximal and distal ends of the balloon, the balloon disposed over the marker bands.

22. The balloon delivery catheter apparatus of claim 16, further comprising a handle received by a proximal end of the catheter tubing, the handle comprising:
a handle base defining a handle lumen therethrough;
a collet received at least partially in the handle lumen at a distal end portion of the handle base, the collet defining a collet lumen therethrough; and
a handle head releasably connected to the distal end portion of the handle base over the collet, the handle head defining an aperture axially aligned with the collet lumen and sized to receive the proximal end of the catheter tubing therethrough and at least partially in the collet lumen;
wherein the handle lumen is in fluid communication with the lumen of the received catheter tubing; and
wherein movement of the handle head toward the handle base causes constriction of the collet about the received catheter tubing.

23. The balloon delivery catheter apparatus of claim 22, wherein the collet comprises:
a substantially tubular section having an outer diameter less than or equal to a diameter of the handle lumen; and
a chuck attached to the substantially tubular section and having an outer diameter larger than the handle lumen, the chuck defining a chamfered surface arranged to engage an opposing chamfered surface of the handle base;

wherein movement of the handle head toward the handle base causes movement of the collet toward the handle base and the chamfered surface of the handle base to exert a substantially radially inward force on the opposing chamfered surface of the chuck.

24. The balloon delivery catheter apparatus of claim 22, wherein the handle head is threadably received by the distal end portion of the handle base.

25. The balloon delivery catheter apparatus of claim 22, wherein the handle further comprises a valve member disposed on a proximal end portion of the handle base.

26. The balloon delivery catheter apparatus of claim 22, wherein the handle further comprises a strain relief disposed on at least one of the handle base and the handle head.

27. A balloon delivery catheter apparatus comprising:
a catheter tubing defining a lumen therethrough;
a balloon disposed near a distal end of the catheter tubing and moving between deflated and inflated states;
a core wire having a proximal end attached near the distal end of the catheter tubing inside the lumen and extending distally away and substantially co-axially with the catheter tubing through the balloon to a distal free end;
proximal and distal balloon control bands concentrically arranged around respective proximal and distal end portions of the balloon, each balloon control band comprising an elastic material that expands during inflation of the balloon and contracts upon deflation of the balloon, the balloon control bands impeding expansion of the proximal and distal end portions of the balloon and assisting deflation of the balloon after balloon inflation;
a coil disposed around the core wire, the coil having a proximal end attached to at least one of the distal end portion of the balloon and the distal balloon control band;
proximal and distal marker bands disposed on the core wire near respective proximal and distal ends of the balloon, the balloon disposed over the marker bands;
a laser activated low density polyethylene bonding portion abutting and interposed between the coil and each of the distal end portion of the balloon and the distal balloon control band, the laser activated low density polyethylene bonding the coil and one or more of the balloon and the distal balloon control band, the laser activated low density polyethylene bonding portion having a first state before laser activation and a second state after activation, wherein the laser activated low density polyethylene bonding portion is unbonded to the coil in the first state and the laser activated low density polyethylene bonding portion is bonded to the coil and extending into spaces defined by the coil in the second state; and
a balloon support tube co-axially disposed over the core wire and the marker bands and within the balloon;
wherein the balloon control bands each have a diametric cross-section larger than the balloon in its uninflated state and an unexpanded stent received over the balloon to impede axial movement of the unexpanded stent off of the balloon; and
wherein the balloon support tube impedes axial movement of the marker bands along the core wire and prevents compression of the balloon below a threshold diameter.

28. The balloon delivery catheter apparatus of claim 27, wherein the proximal and distal balloon control bands are secured to the respective proximal and distal end portions of the balloon.

29. The balloon delivery catheter apparatus of claim 27, wherein the proximal end portion of the balloon and the proximal balloon control band are both attached to the catheter tubing.

30. The balloon delivery catheter apparatus of claim 27, wherein each balloon control band has a non-uniform cross-sectional thickness along an axial direction of the balloon control band.

31. The balloon delivery catheter apparatus of claim 30, wherein each balloon control band has first and second end portions, the first end portion having a larger diametric cross-section than the second end portion, the first end portion of each balloon control band disposed adjacent to a received stent on the balloon.

32. The balloon delivery catheter apparatus of claim 27, wherein the balloon and the balloon control bands are coaxially disposed about the core wire.

33. The balloon delivery catheter apparatus of claim 27, wherein the balloon control bands restrict expansion of at least the end portions of the balloon to a threshold diameter.

34. The balloon delivery catheter apparatus of claim 27, wherein the balloon support tube prevents compression of a received stent over the balloon to a diameter less than a threshold un-deployed stent diameter.

35. The balloon delivery catheter apparatus of claim 27, wherein the balloon support tube has an axial length less than or equal to an axial length of the balloon.

36. The balloon delivery catheter apparatus of claim 27, wherein the balloon support tube is attached to the core wire so that a proximal end of the balloon support tube is approximately concentric with a proximal end of the balloon, and a distal end of the balloon support tube is approximately concentric with a distal end of the balloon.

37. The balloon delivery catheter apparatus of claim 27, wherein the balloon support tube comprises a polyamide material.

38. The balloon delivery catheter apparatus of claim 27, wherein the balloon support tube prevents an inner surface of the balloon from contacting an outer radial surface of each of the marker bands.

39. The balloon delivery catheter apparatus of claim 27, wherein the coil extends beyond the distal end portion of the balloon.

40. The balloon delivery catheter apparatus of claim 27, further comprising a handle received by a proximal end of the catheter tubing, the handle comprising:
a handle base defining a handle lumen therethrough;
a collet received at least partially in the handle lumen at a distal end portion of the handle base, the collet defining a collet lumen therethrough; and
a handle head releasably connected to the distal end portion of the handle base over the collet, the handle head defining an aperture axially aligned with the collet lumen and sized to receive the proximal end of the catheter tubing therethrough and at least partially in the collet lumen;
wherein the handle lumen is in fluid communication with the lumen of the received catheter tubing; and
wherein movement of the handle head toward the handle base causes constriction of the collet about the received catheter tubing.

41. The balloon delivery catheter apparatus of claim 40, wherein the collet comprises:
a substantially tubular section having an outer diameter less than or equal to a diameter of the handle lumen; and
a chuck attached to the substantially tubular section and having an outer diameter larger than the handle lumen, the chuck defining a chamfered surface arranged to engage an opposing chamfered surface of the handle base;

wherein movement of the handle head toward the handle base causes movement of the collet toward the handle base and the chamfered surface of the handle base to exert a substantially radially inward force on the opposing chamfered surface of the chuck.

42. The balloon delivery catheter apparatus of claim 40, wherein the handle head is threadably received by the distal end portion of the handle base.

43. The balloon delivery catheter apparatus of claim 40, wherein the handle further comprises a valve member disposed on a proximal end portion of the handle base.

44. The balloon delivery catheter apparatus of claim 40, wherein the handle further comprises a strain relief disposed on at least one of the handle base and the handle head.

45. A method of manufacturing a medical device, the method comprising:

disposing a proximal end of a core wire near a distal end of a catheter tubing inside a lumen defined by the catheter tubing;

disposing a balloon near the distal end of a catheter tubing and over the core wire, the balloon being movable between deflated and inflated states, the core wire extending distally away and substantially co-axially with the catheter tubing through the balloon to a distal free end;

disposing proximal and distal balloon control bands concentrically around respective proximal and distal end portions of the balloon, each balloon control band comprising an elastic material that expands during inflation of the balloon and contracts upon deflation of the balloon, the balloon control bands impeding expansion of the proximal and distal end portions of the balloon and assisting deflation of the balloon after balloon inflation;

attaching a proximal end of a coil to at least one of the distal end portion of the balloon and the distal balloon control band, the coil extending around the core wire;

bonding the coil to each of the distal end portion of the balloon, the distal control band, and the balloon using a laser activated low density polyethylene bonding portion, the laser activated low density polyethylene bonding portion existing in a first state where the bonding portion is unbonded to the coil and a second state where the bonding portion is bonded to the coil and extending into spaces defined by the coil;

laser activating the bonding portion from the first state to the second state, thereby reshaping the bonding portion such that the bonding portion is interposed between the coil and each of the distal end portion of the balloon and the distal control band; and co-axially disposing a balloon support tube over the core wire and within the balloon;

wherein the balloon support tube prevents compression of the balloon below a threshold diameter; and wherein the balloon control bands each have a diametric cross-section larger than the balloon in its uninflated state and an unexpanded stent received over the balloon to impede axial movement of the unexpanded stent off of the balloon.

46. The method of claim 45, further comprising at least partially securing the proximal and distal balloon control bands to the respective proximal and distal end portions of the balloon.

47. The method of claim 45, further comprising affixing the proximal end portion of the balloon and the proximal balloon control band both to the catheter tubing.

48. The method of claim 45, further comprising shaping the balloon control bands to have a non-uniform cross-sectional thickness along an axial direction of the balloon control band.

49. The method of claim 45, wherein each balloon control band has first and second end portions, the first end portion having a larger diametric cross-section than the second end portion, the method further comprising arranging the first end portion of each balloon control band adjacent to a received stent on the balloon.

50. The method of claim 45, further comprising extending the core wire beyond the distal end portion of the balloon.

51. The method of claim 45, further comprising coaxially disposing the balloon and the balloon control bands about the core wire.

52. The method of claim 45, wherein the balloon control bands restrict expansion of at least the end portions of the balloon to a threshold diameter.

53. A method of manufacturing a medical device, the method comprising:

disposing a proximal end of a core wire near a distal end of a catheter tubing inside a lumen defined by the catheter tubing;

disposing a balloon near a distal end of a catheter tubing, the balloon being movable between deflated and inflated states, the core wire extending distally away and substantially co-axially with the catheter tubing through the balloon to a distal free end;

attaching a proximal end of a coil to at least one of the distal end portion of the balloon and a distal balloon control band, the coil extending around the core wire;

bonding the coil to each of the distal end portion of the balloon, the distal control band, and the balloon using a laser activated low density polyethylene bonding portion, the laser activated low density polyethylene bonding portion existing in a first state where the bonding portion is unbonded to the coil and a second state where the bonding portion is bonded to the coil and extending into spaces defined by the coil;

laser activating the bonding portion from the first state to the second state, thereby reshaping the bonding portion such that the bonding portion is interposed between the coil and each of the distal end portion of the balloon and the distal control band; and co-axially disposing a balloon support tube over the core wire and within the balloon;

wherein the balloon support tube prevents compression of the balloon below a threshold diameter.

54. The method of claim 53, further comprising coining a length of material to form the core wire.

55. The method of claim 53, wherein the balloon support tube prevents compression of a received stent over the balloon to a diameter less than a threshold un-deployed stent diameter.

56. The method of claim 53, further comprising sizing the balloon support tube to have an axial length less than or equal to an axial length of the balloon.

57. The method of claim 53, further comprising affixing the balloon support tube to the core wire so that a proximal end of the balloon support tube is approximately concentric with a proximal end of the balloon, and a distal end of the balloon support tube is approximately concentric with a distal end of the balloon.

58. The method of claim 53, wherein the balloon support tube comprises a polyamide material.

59. The method of claim 53, further comprising:
disposing proximal and distal marker bands on the core wire near respective proximal and distal ends of the balloon, the balloon disposed over the marker bands; and
co-axially disposing the balloon support tube over the core wire and the marker bands and within the balloon;
wherein the balloon support tube impedes axial movement of the marker bands along the core wire.

60. The method of claim 59, wherein the balloon support tube prevents an inner surface of the balloon from contacting an outer radial surface of each of the marker bands.

61. A method of manufacturing a medical device, the method comprising:
disposing a proximal end of a core wire near a distal end of a catheter tubing inside a lumen defined by the catheter tubing;
disposing a balloon near the distal end of a catheter tubing and over the core wire, the balloon being movable between deflated and inflated states, the core wire extending distally away and substantially co-axially with the catheter tubing through the balloon to a distal free end;
disposing proximal and distal marker bands on the core wire near respective proximal and distal ends of the balloon, the balloon disposed over the marker bands; and
co-axially disposing a balloon support tube over the core wire and the marker bands and within the balloon;
disposing proximal and distal balloon control bands concentrically around respective proximal and distal end portions of the balloon, each balloon control band comprising an elastic material that expands during inflation of the balloon and contracts upon deflation of the balloon, the balloon control bands impeding expansion of the proximal and distal end portions of the balloon and assisting deflation of the balloon after balloon inflation;
attaching a proximal end of a coil to at least one of the distal end portion of the balloon and the distal balloon control band, the coil extending around the core wire;
bonding the coil to each of the distal end portion of the balloon, the distal control band, and the balloon using a laser activated low density polyethylene bonding portion, the laser activated low density polyethylene bonding portion existing in a first state where the bonding portion is unbonded to the coil and a second state where the bonding portion is bonded to the coil and extending into spaces defined by the coil; and
laser activating the bonding portion from the first state to the second state, thereby reshaping the bonding portion such that the bonding portion is interposed between the coil and each of the distal end portion of the balloon and the distal control band;
wherein the balloon support tube prevents compression of the balloon below a threshold diameter and impedes axial movement of the marker bands along the core wire; and
wherein the balloon control bands each have a diametric cross-section larger than the balloon in its uninflated state and an unexpanded stent received over the balloon to impede axial movement of the unexpanded stent off of the balloon.

62. The method of claim 61, further comprising attaching a proximal end of the coil to at least one of the distal end portion of the balloon and the distal balloon control band.

63. The method of claim 61, further comprising securing the proximal and distal balloon control bands to the respective proximal and distal end portions of the balloon.

64. The method of claim 61, further comprising affixing the proximal end portion of the balloon and the proximal balloon control band both to the catheter tubing.

65. The method of claim 61, further comprising shaping the balloon control bands to have a non-uniform cross-sectional thickness along an axial direction of the balloon control band.

66. The method of claim 65, wherein each balloon control band has first and second end portions, the first end portion having a larger diametric cross-section than the second end portion, the method further comprising arranging the first end portion of each balloon control band adjacent to a received stent on the balloon.

67. The method of claim 61, further comprising extending the core wire beyond the distal end portion of the balloon.

68. The method of claim 61, further comprising coaxially disposing the balloon and the balloon control bands about the core wire.

69. The method of claim 61, wherein the balloon control bands restrict expansion of at least the end portions of the balloon to a threshold diameter.

70. The method of claim 61, wherein the balloon support tube prevents compression of a received stent over the balloon to a diameter less than a threshold un-deployed stent diameter.

71. The method of claim 61, further comprising sizing the balloon support tube to have an axial length less than or equal to an axial length of the balloon.

72. The method of claim 61, further comprising affixing the balloon support tube to the core wire so that a proximal end of the balloon support tube is approximately concentric with a proximal end of the balloon, and a distal end of the balloon support tube is approximately concentric with a distal end of the balloon.

73. The method of claim 61, wherein the balloon support tube comprises a polyamide material.

74. The method of claim 61, wherein the balloon support tube prevents an inner surface of the balloon from contacting an outer radial surface of each of the marker bands.

75. A method of treating vascular stenosis, the method comprising:
inserting into a vessel of a patient a portion of a balloon delivery catheter apparatus, the balloon delivery catheter apparatus comprising:
a catheter tubing defining a lumen therethrough;
a balloon disposed near a distal end of the catheter tubing and moving between deflated and inflated states;
a core wire having a proximal end attached near the distal end of the catheter tubing inside the lumen and extending distally away and substantially co-axially with the catheter tubing through the balloon to a distal free end;
proximal and distal balloon control bands concentrically arranged around respective proximal and distal end portions of the balloon, each balloon control band comprising an elastic material that expands during inflation of the balloon and contracts upon deflation of the balloon, the balloon control bands impeding expansion of the proximal and distal end portions of the balloon and assisting deflation of the balloon after balloon inflation;
a coil disposed around the core wire, the coil having a proximal end attached to at least one of the distal end portion of the balloon and the distal balloon control band;

a laser activated low density polyethylene bonding portion abutting and interposed between the coil and each of the distal end portion of the balloon and the distal balloon control band, the laser activated low density polyethylene bonding the coil and one or more of the balloon and the distal balloon control band, the laser activated low density polyethylene bonding portion having a first state before laser activation and a second state after activation, wherein in the first state the bonding portion is unbonded to the coil and in the second state the bonding portion is bonded to the coil and extending into spaces defined by the coil;

proximal and distal marker bands disposed on the core wire near respective proximal and distal ends of the balloon, the balloon disposed over the marker bands; and a balloon support tube co-axially disposed over the core wire and the marker bands and within the balloon;

wherein the balloon control bands each have a diametric cross-section larger than the balloon in its uninflated state and an unexpanded stent received over the balloon to impede axial movement of the unexpanded stent off of the balloon; and wherein the balloon support tube impedes axial movement of the marker bands along the core wire and prevents compression of the balloon below a threshold diameter;

advancing the balloon across the vascular stenosis;

inflating the balloon to compress the vascular stenosis;

deflating the balloon; and removing the balloon delivery catheter apparatus from the patient.

\* \* \* \* \*